(12) United States Patent
Gao et al.

(10) Patent No.: US 11,359,058 B2
(45) Date of Patent: Jun. 14, 2022

(54) PROCESSES AND SYSTEMS FOR PREPARING CELLULAR OR VIRAL MEMBRANES AND NANOPARTICLES

(71) Applicant: ARYTHA BIOSCIENCES, LLC, San Diego, CA (US)

(72) Inventors: Weiwei Gao, La Jolla, CA (US); Che-Ming Jack Hu, Taipei (TW)

(73) Assignee: ARYTHA BIOSCIENCES, LLC, San Diego, CA (US)

( * ) Notice: Subject to any disclaimer, the term of this patent is extended or adjusted under 35 U.S.C. 154(b) by 451 days.

(21) Appl. No.: 15/777,208

(22) PCT Filed: Nov. 18, 2016

(86) PCT No.: PCT/US2016/062935
§ 371 (c)(1),
(2) Date: May 17, 2018

(87) PCT Pub. No.: WO2017/087897
PCT Pub. Date: May 26, 2017

(65) Prior Publication Data
US 2019/0382539 A1    Dec. 19, 2019

Related U.S. Application Data

(60) Provisional application No. 62/257,161, filed on Nov. 18, 2015.

(51) Int. Cl.
| | |
|---|---|
| *C08J 3/12* | (2006.01) |
| *B01D 61/14* | (2006.01) |
| *C12N 5/00* | (2006.01) |
| *C12N 5/078* | (2010.01) |
| *B01D 63/02* | (2006.01) |
| *B82Y 40/00* | (2011.01) |

(52) U.S. Cl.
CPC .............. *C08J 3/12* (2013.01); *B01D 61/142* (2013.01); *C12N 5/0006* (2013.01); *C12N 5/0087* (2013.01); *C12N 5/0641* (2013.01); *B01D 63/02* (2013.01); *B01D 2315/16* (2013.01); *B82Y 40/00* (2013.01); *C08J 2367/04* (2013.01); *C08J 2377/04* (2013.01)

(58) Field of Classification Search
None
See application file for complete search history.

(56) References Cited

U.S. PATENT DOCUMENTS

| | | | |
|---|---|---|---|
| 5,490,937 | A | 2/1996 | van Reis |
| 8,759,294 | B2 | 6/2014 | Egea et al. |
| 8,889,103 | B2 | 11/2014 | Hay et al. |
| 2013/0037977 | A1 | 2/2013 | Burke et al. |
| 2013/0337066 | A1 | 12/2013 | Zhang et al. |

| | | | |
|---|---|---|---|
| 2014/0256818 | A1 | 9/2014 | Leung et al. |
| 2015/0343332 | A1 | 12/2015 | Boyd et al. |
| 2017/0000875 | A1 | 1/2017 | Hu |

FOREIGN PATENT DOCUMENTS

| | | |
|---|---|---|
| CN | 103857387 A | 6/2014 |
| WO | 2013052167 A2 | 4/2013 |

OTHER PUBLICATIONS

Fang, et al. (2014) "Cancer Cell Membrane-Coated Nanoparticles for Anticancer Vaccination and Drug Delivery", NanoLetters, 14: 2181-88.*
Valencia, et al. (2010) "Single-Step Assembly of Homogenous Lipid-Polymeric and Lipid-Quantum Dot Nanoparticles Enabled by Microfluidic Rapid Mixing", ACS Nano, 4(3): 1671-79. (Year: 2010).*
Search Report for Chinese patent application CN201680078779.6, dated Jun. 15, 2020, 2 pages.
1st Office Action for Chinese patent application CN201680078779.6, dated Jun. 29, 2020, 10 pages with extra 6 pages of English language equivalent or summary.
International Search Report for international patent application PCT/US2016/062935 (WO2017087897), dated Feb. 6, 2017, 3 pages.
Written Opinion of the International Searching Authority for international patent application PCT/US2016/062935 (WO2017087897), dated Feb. 6, 2017, 6 pages.
International Preliminary Report on Patentability for international patent application PCT/US2016/062935 (WO2017087897), dated May 22, 2018, 7 pages.
Response to 1st Office Action for Chinese patent application CN201680787796, dated Jan. 14, 2021, 31 pages.
Claim Amendments (marked-up version) in Response to 1st Office Action for Chinese patent application CN2016800787796, dated Jan. 14, 2021, 16 pages.
2nd Office Action for Chinese patent application CN201680078779.6, dated May 14, 2021, 3 pages with extra 5 pages of English language equivalent or summery.
Response to 2nd Office Action for Chinese patent application CN201680078779.6, dated Jul. 27, 2021, 27 pages.
Supplemental Amendments to 2nd Office Action for Chinese patent application CN201680078779.6, dated Sep. 23, 2021, 26 pages.
2nd Supplemental Response to 2nd Office Action for Chinese patent application CN201680078779.6, dated Oct. 12, 2021, 26 pages.
Notice of Registration Procedures for Chinese patent application CN201680078779.6, dated Oct. 25, 2021, 2 pages.
Notice to Grant the Patent Right for Chinese patent application CN201680078779.6, dated Oct. 25, 2021, 2 pages.

* cited by examiner

*Primary Examiner* — Robert M Kelly
(74) *Attorney, Agent, or Firm* — Rimon, P.C.

(57) ABSTRACT

The present invention relates to processes and systems for preparing nanoparticles, cellular or viral membranes and/or cellular or viral membrane coated nanoparticles using or comprising, inter alia, a multi-inlet vortexing reactor, tangential flow filtration (TFF) and/or a high shear fluid processor such as a microfluidizer (or a microfluidizer processor). The present invention also relates to the nanoparticles, cellular or viral membranes and/or cellular or viral membrane coated nanoparticles prepared by the present processes and systems, and the uses and/or applications of the nanoparticles, cellular or viral membranes and/or cellular or viral membrane coated nanoparticles.

10 Claims, 18 Drawing Sheets

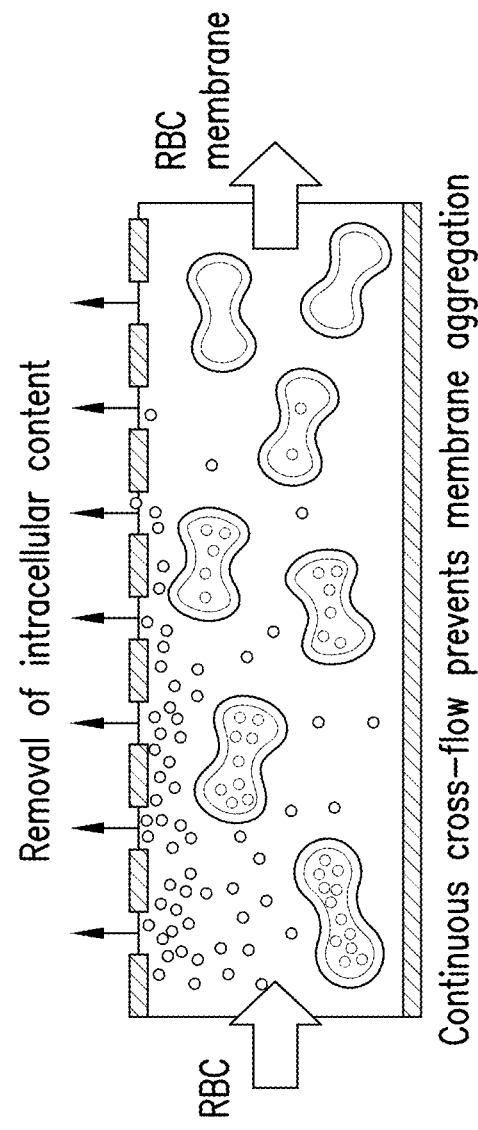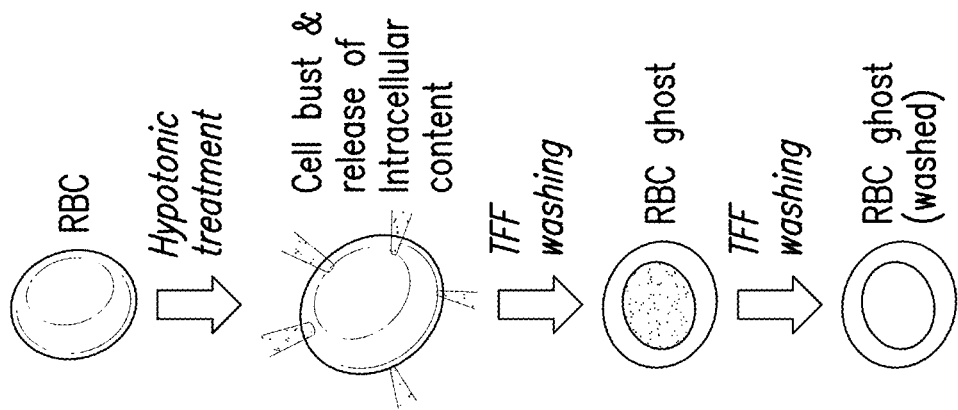
FIG.9B
FIG.9A

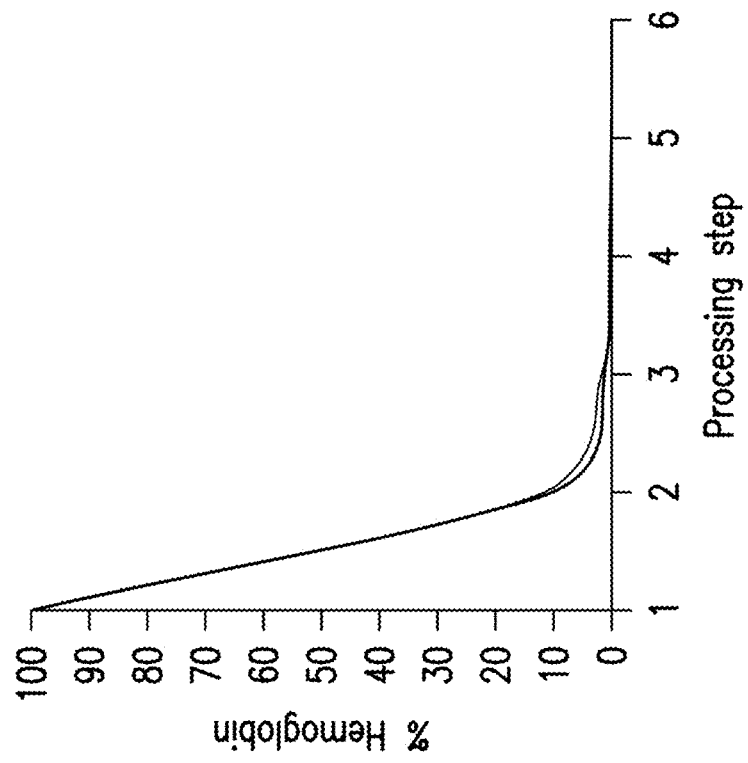
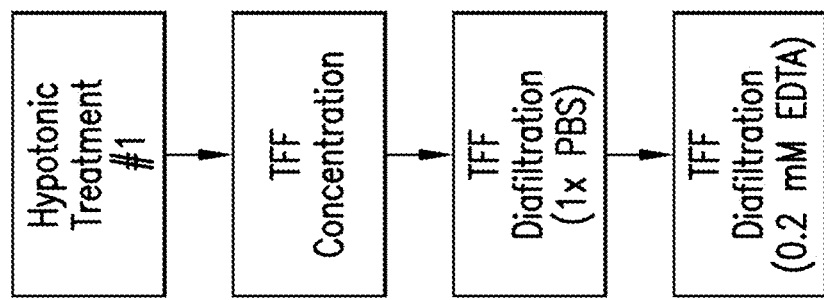
FIG.11A FIG.11B FIG.11C
Processing step:
1. 400 mL hypotonic solution.
2. End of concentrating step to 40 mL.
3. End of 2 diafiltrations w/ 1X PBS.
4. End of 5 diafiltrations w/ 1X PBS.
5. End of 2 diafiltrations w/ 0.2mM EDTA.
6. End of 5 diafiltrations w/ 0.2mM EDTA.

Nanosponges (10 mg/mL in sucrose)

|          | In water | In PBS |
|----------|----------|--------|
| Diameter | 86.56    | 99.3   |
| PDI      | 0.16     | 0.13   |

US 11,359,058 B2

PROCESSES AND SYSTEMS FOR PREPARING CELLULAR OR VIRAL MEMBRANES AND NANOPARTICLES

CROSS-REFERENCE TO RELATED APPLICATION

This application is a U.S. National Phase filing of International Patent Application No. PCT/US2016/062935, entitled "Processes and Systems for Preparing Cellular or Viral Membranes and Nanoparticles," having an international filing date of Nov. 18, 2016, which claims priority to U.S. Provisional Application No. 62/257,161, filed Nov. 18, 2015; the contents of each of these applications are incorporated herein by reference in their entireties for all purposes.

STATEMENT REGARDING FEDERALLY SPONSORED RESEARCH

This invention was made with Government support under National Science Foundation (NSF) Grant No. 1456104. The Government has certain rights in the invention.

FIELD

The present invention relates to processes and systems for preparing nanoparticles, cellular or viral membranes and/or cellular or viral membrane coated nanoparticles using or comprising, inter alia, a multi-inlet vortexing reactor, tangential flow filtration (TFF) and/or a high shear fluid processor such as a microfluidizer (or a microfluidizer processor). The present invention also relates to the nanoparticles, cellular or viral membranes and/or cellular or viral membrane coated nanoparticles prepared by the present processes and systems, and the uses and/or applications of the nanoparticles, cellular or viral membranes and/or cellular or viral membrane coated nanoparticles.

SUMMARY

In one aspect, the present invention provides for a process for preparing a nanoparticle, which process comprises: 1) mixing a material for forming a nanoparticle in an organic solvent and an aqueous phase using a multi-inlet vortexing reactor to form a composition comprising said nanoparticle; and 2) subjecting said composition to tangential flow filtration (TFF) to reduce the amount of or to remove said organic solvent from said composition. In another aspect, the present invention provides for a system for preparing a nanoparticle, which system comprises: 1) a multi-inlet vortexing reactor that is configured to mix a material for forming a nanoparticle in an organic solvent and an aqueous phase to form a composition comprising said nanoparticle; and 2) a tangential flow filtration (TFF) system that is configured to reduce the amount of or to remove said organic solvent from said composition. A nanoparticle prepared by the above process and system is also provided.

In still another aspect, the present invention provides for a process for preparing a cellular or viral membrane, which process comprises: 1) lysing a cell, a cellular vesicle or a virus to obtain a composition comprising a cellular or viral membrane and a non-membrane cellular or viral moiety; and 2) subjecting said composition to tangential flow filtration (TFF) to separate said cellular or viral membrane from said non-membrane cellular or viral moiety. In yet another aspect, the present invention provides for a system for preparing a cellular or viral membrane, which system comprises: 1) means for lysing a cell, a cellular vesicle or a virus to obtain a composition comprising a cellular or viral membrane and a non-membrane cellular or viral moiety; and 2) a tangential flow filtration (TFF) system that is configured to separate said cellular or viral membrane from said non-membrane cellular or viral moiety. A cellular or viral membrane prepared by the above process and system is also provided.

In yet another aspect, the present invention provides for a process for preparing a cellular or viral membrane coated nanoparticle, which process comprises mixing a nanoparticle inner core comprising a non-cellular material with a cellular membrane derived from a cell or a membrane derived from a virus using a high shear fluid processor to form a nanoparticle comprising said inner core and an outer surface comprising said cellular membrane or viral membrane. In yet another aspect, the present invention provides for a system for preparing a cellular or viral membrane coated nanoparticle, which system comprises: 1) a system for preparing a nanoparticle core, which system comprises: a) a multi-inlet vortexing reactor that is configured to mix a material for forming a nanoparticle core in an organic solvent and an aqueous phase to form a composition comprising said nanoparticle core; and b) a tangential flow filtration (TFF) system that is configured to reduce the amount of or to remove said organic solvent from said composition; 2) a system for preparing a cellular or viral membrane, which system comprises: a) means for lysing a cell, a cellular vesicle or a virus to obtain a composition comprising a cellular or viral membrane and a non-membrane cellular or viral moiety; and b) a tangential flow filtration (TFF) system that is configured to separate said cellular or viral membrane from said non-membrane cellular or viral moiety; and 3) a high shear fluid processor that is configured to mix said nanoparticle inner core comprising said material with said cellular membrane derived from a cell or a membrane derived from a virus to form a nanoparticle comprising said inner core and an outer surface comprising said cellular membrane or viral membrane. A cellular or viral membrane coated nanoparticle prepared by the above process and system is also provided. Various compositions comprising the cellular or viral membrane coated nanoparticle and uses of the cellular or viral membrane coated nanoparticle are further provided.

In some aspects, the prevent disclosure relates to U.S. application Ser. No. 13/827,906, filed Mar. 14, 2013, International Application No. PCT/US2012/039411, filed May 24, 2012 and published as WO 2013/052167 A2 and U.S. provisional application Ser. No. 61/492,626, filed Jun. 2, 2011. The contents of the above applications are incorporated by reference in their entireties.

BRIEF DESCRIPTION OF THE DRAWINGS

FIG. 11 illustrates (A) through the process optimization, 2 of the 3 hypotonic treatments in previous process can be eliminated. The change has significant simplified the process. Purified membrane can be produce by using only 1 hypotonic treatment. (B) Removal of hemoglobin from RBCs in different checkpoints during the process. (C) Appearance of RBC and purified RBC membrane.

DETAILED DESCRIPTION OF THE INVENTION

Figure 1:
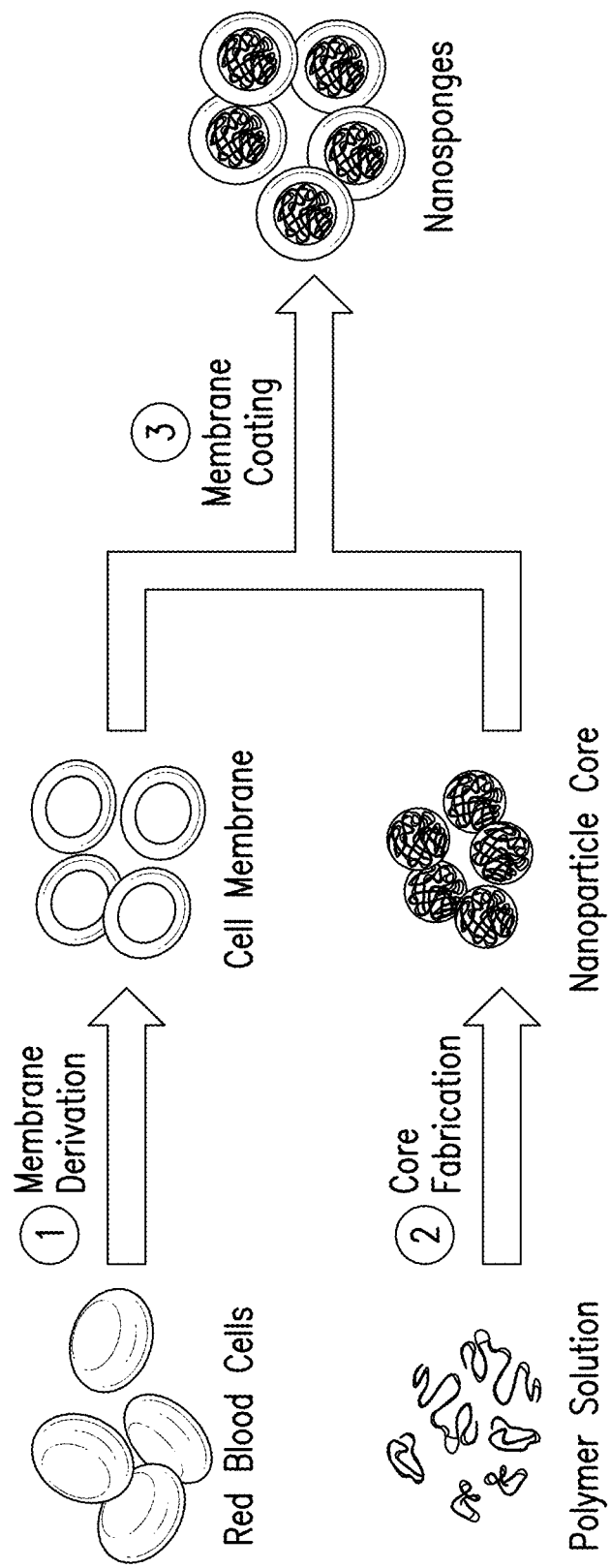
FIG. 1 illustrates a flow diagram of an exemplary cellular or viral membrane coated nanoparticle (nanosponge) production processes. Each major component, including nanoparticle core preparation, red blood cell membrane purification, and particle-membrane fusion, can be individually optimized for process integration. The process can be divided into three steps: (1) membrane derivation, where red blood cells (RBCs) go through hypotonic treatment to release intracellular content and the membrane is isolated with tangential flow filtration (TFF); (2) core fabrication, where the nanosponge cores are made from dissolving polymers in organic solvent followed by solvent replacement with TFF; and (3) membrane coating, achieved by high shear processing using homogenizer such as amicrofluidizer.

The practice of the present invention will employ, unless otherwise indicated, conventional techniques of nanotechnology, nano-engineering, molecular biology (including recombinant techniques), microbiology, cell biology, biochemistry, immunology, and pharmacology, which are within the skill of the art. Such techniques are explained fully in the literature, such as, *Molecular Cloning: A Laboratory Manual, 2nd ed.* (Sambrook et al., 1989); *Oligonucleotide Synthesis* (M. J. Gait, ed., 1984); *Animal Cell Culture* (R. I. Freshney, ed., 1987); *Methods in Enzymology* (Academic Press, Inc.); *Current Protocols in Molecular Biology* (F. M. Ausubel et al., eds., 1987, and periodic updates); *PCR: The Polymerase Chain Reaction* (Mullis et al., eds., 1994); and Remington, *The Science and Practice of Pharmacy, 22$^{th}$ ed.*, (Pharmaceutical Press and Philadelphia College of Pharmacy at University of the Sciences 2012).

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

A. Definitions

100241 To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and Bin combination. The expression "A, Band/or C" is intended to mean A alone, B alone, C alone, A and B in combination, A and C in combination, B and C in combination or A, B, and C in combination.

Cellular Membrane: The term "cellular membrane" as used herein refers to a biological membrane enclosing or separating structure acting as a selective barrier, within or around a cell or an emergent viral particle. The cellular membrane is selectively permeable to ions and organic molecules and controls the movement of substances in and out of cells. The cellular membrane comprises a phospholipid uni- or bilayer, and optionally associated proteins and carbohydrates. As used herein, the cellular membrane refers to a membrane obtained from a naturally occurring biological membrane of a cell or cellular organelles, or one derived therefrom. As used herein, the term "naturally occurring" refers to one existing in nature. As used herein, the term "derived therefrom" refers to any subsequent modification of the natural membrane, such as isolating the cellular membrane, creating portions or fragments of the membrane, removing and/or adding certain components, such as lipid, protein or carbohydrates, from or into the membrane taken from a cell or a cellular organelle. A membrane can be derived from a naturally occurring membrane by any suitable methods. For example, a membrane can be prepared or isolated from a cell or a virus and the prepared or isolated membrane can be combined with other substances or materials to form a derived membrane. In another example, a cell or virus can be recombinantly engineered to produce "non-natural" substances that are incorporated into its membrane in vivo, and the cellular or viral membrane can be prepared or isolated from the cell or the virus to form a derived membrane.

In various embodiments, the cellular membrane covering either of the unilamellar or multilamellar nanoparticles can be further modified to be saturated or unsaturated with other lipid components, such as cholesterol, free fatty acids, and phospholipids, also can include endogenous or added proteins and carbohydrates, such as cellular surface antigen. In such cases, an excess amount of the other lipid components can be added to the membrane wall which will shed until the concentration in the membrane wall reaches equilibrium, which can be dependent upon the nanoparticle environment. Membranes may also comprise other agents that may or may not increase an activity of the nanoparticle. In other examples, functional groups such as antibodies and aptamers can be added to the outer surface of the membrane to enhance site targeting, such as to cell surface epitopes found in cancer cells. The membrane of the nanoparticles can also comprise particles that can be biodegradable, cationic nanoparticles including, but not limited to, gold, silver, and synthetic nanoparticles.

Synthetic or artificial membrane: As used herein, the term "synthetic membrane" or "artificial membrane" refers to a man-made membrane that is produced from organic material, such as polymers and liquids, as well as inorganic materials. A wide variety of synthetic membranes are well known in the art.

Nanoparticle: The term "nanoparticle" as used herein refers to nanostructure, particles, vesicles, or fragments thereof having at least one dimension (e.g., height, length, width, or diameter) of between about 1 nm and about 10 µm. For systemic use, an average diameter of about 50 nm to about 500 nm, or 100 nm to 250 nm may be preferred. The term "nanostructure" includes, but is not necessarily limited to, particles and engineered features. The particles and engineered features can have, for example, a regular or irregular shape. Such particles are also referred to as nanoparticles. The nanoparticles can be composed of organic materials or other materials, and can alternatively be implemented with porous particles. The layer of nanoparticles can be implemented with nanoparticles in a monolayer or with a layer having agglomerations of nanoparticles. In some embodiments, the nanoparticle comprising or consisting an inner core covered by an outer surface comprising the membrane as discussed herein. The invention contemplates any nanoparticles now known and later developed that can be coated with the membrane described herein.

Pharmaceutically active: The term "pharmaceutically active" as used herein refers to the beneficial biological activity of a substance on living matter and, in particular, on cells and tissues of the human body. A "pharmaceutically active agent" or "drug" is a substance that is pharmaceutically active and a "pharmaceutically active ingredient" (API) is the pharmaceutically active substance in a drug.

Pharmaceutically acceptable: The term "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

Pharmaceutically acceptable salt: The term "pharmaceutically acceptable salt" as used herein refers to acid addition salts or base addition salts of the compounds, such as the multi-drug conjugates, in the present disclosure. A pharmaceutically acceptable salt is any salt which retains the activity of the parent nanoparticle or compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zurich, 2002; Berge et al., J Pharm. Sci. 66: 1, 1977). In some embodiments, a "pharmaceutically acceptable salt" is intended to mean a salt of a free acid or base of a nanoparticle or compound represented herein that is non-toxic, biologically tolerable, or otherwise biologically suitable for administration to the subject. See, generally, Berge, et al., J. Pharm. Sci., 1977, 66, 1-19. Preferred pharmaceutically acceptable salts are those that are pharmacologically effective and suitable for contact with the tissues of subjects without undue toxicity, irritation, or allergic response. A nanoparticle or compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, [gamma]-hydroxybutyrates, glycolates, tartrates, and mandelates.

Pharmaceutically acceptable carrier: The term "pharmaceutically acceptable carrier" as used herein refers to an excipient, diluent, preservative, solubilizer, emulsifier, adjuvant, and/or vehicle with which a nanoparticle or compound, such as a multi-drug conjugate, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy. 20''' ed., (Lippincott, Williams & Wilkins 2003). Except insofar as any conventional media or agent is incompatible with the active compound, such use in the compositions is contemplated.

Phospholipid: The term "phospholipid", as used herein, refers to any of numerous lipids contain a diglyceride, a phosphate group, and a simple organic molecule such as choline. Examples of phospholipids include, but are not limited to, Phosphatide acid (phosphatidate) (PA), Phosphatidylethanolamine (cephalin) (PE), Phosphatidylcholine (lecithin) (PC), Phosphatidylserine (PS), and Phosphoinositides which include, but are not limited to, Phosphatidylinositol (P1), Phosphatidylinositol phosphate (PIP), Phosphatidylinositol bisphosphate (PIP2) and Phosphatidylinositol triphosphate (P1P3). Additional examples of PC include DDPC, DLPC, DMPC, DPPC, DSPC, DOPC, POPC, DRPC, and DEPC as defined in the art.

Therapeutically Effective Amount: As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. More specific embodiments are included in the Pharmaceutical Preparations and Methods of Administration section below. In some embodiments, the term "therapeutically effective amount" or "effective amount" refers to an amount of a therapeutic agent that when administered alone or in combination with an additional therapeutic agent to a cell, tissue, or subject is effective to prevent or ameliorate the disease or condition such as a hemolytic disease or condition, or the progression of the disease or condition. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. Reduction of the signs or symptoms of a disease may also be felt by the patient. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

As used herein, "preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition.

The term "combination" refers to either a fixed combination in one dosage unit form, or a kit of parts for the combined administration where a nanoparticle or compound and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a nanoparticle or compound and a combination partner, are both administered to a patient simultaneously in the form of a single entity or dosage. The term "non-fixed combination" means that the active ingredients, e.g., a nanoparticle or compound and a combination partner, are both administered to a patient as separate entities either simultaneously, concurrently or sequentially with no specific time limits, wherein such administration provides therapeutically effective levels of the two moieties or compounds in the body of the patient. The latter also applies to cocktail therapy, e.g., the administration of three or more active ingredients.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, a subject in need refers to an animal, a non-human mammal or a human. As used herein, "animals" include a pet, a farm animal, an economic animal, a sport animal and an experimental animal, such as a cat, a dog, a horse, a cow, an ox, a pig, a donkey, a sheep, a lamb, a goat, a mouse, a rabbit, a chicken, a duck, a goose, a primate, including a monkey and a chimpanzee.

Other objects, advantages and features of the present invention will become apparent from the following specification taken in conjunction with the accompanying drawings.

B. Processes and Systems for Preparing a Nanoparticle

In one aspect, the present invention provides for a process for preparing a nanoparticle, which process comprises: 1) mixing a material for forming a nanoparticle in an organic solvent and an aqueous phase using a multi-inlet vortexing reactor to form a composition comprising said nanoparticle; and 2) subjecting said composition to tangential flow filtration (TFF) to reduce the amount of or to remove said organic solvent from said composition. In another aspect, the present invention provides for a system for preparing a nanoparticle, which system comprises: 1) a multi-inlet vortexing reactor that is configured to mix a material for forming a nanoparticle in an organic solvent and an aqueous phase to form a composition comprising said nanoparticle; and 2) a tangential flow filtration (TFF) system that is configured to reduce the amount of or to remove said organic solvent from said composition.

Any suitable material can be used in the present processes and systems. For example, the material can be a polymer. In one embodiment, the polymer can be a hydrophobic polymer that coils when switched from an organic solvent to an aqueous phase, e.g., water. In another embodiment, the polymer is poly(lactic-co-glycolic acid) (PLGA), polylactic acid (PLA), polyglycolic acid (PGA), polycaprolactone (PCL), polylysine, or polyglutamic acid. In one preferred embodiment, the polymer is poly(lactic-c-glycolic acid) (PLGA). The material can be used at any suitable level. For example, the material can be used at a level ranging from about 0.01 mg/mL to about 40 mg/mL, e.g., at about 0.01 mg/mL, 0.05 mg/mL, 0.1 mg/mL, 0.5 mg/mL, 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 15 mg/mL, 20 mg/mL, 25 mg/mL, 30 mg/mL, 35 mg/mL, or 40 mg/mL of the material, or any sub-range within about 0.01 mg/mL to about 40 mg/mL, e.g., any range between any two of the above levels.

Any suitable organic solvent can be used in the present processes and systems. For example, the organic solvent can be configured to dissolve the material, e.g., a polymer, and miscible with water, such as acetonitrile and acetone. In one embodiment, the organic solvent is acetonitrile. The organic solvent can be used at any suitable level. For example, the organic solvent can be used at a level ranging from about 1% (v/v) to about 50% (v/v), e.g., 1% (v/v), 2% (v/v), 3% (v/v), 4% (v/v), 5% (v/v), 6% (v/v), 7% (v/v), 8% (v/v), 9% (v/v), 10% (v/v), 15% (v/v), 20% (v/v), 25% (v/v), 30% (v/v), 35% (v/v), 40% (v/v), 45% or 50% (v/v) of the organic solvent, or any sub-range within about 1% (v/v) to about 50% (v/v), e.g., any range between any two of the above levels.

Any suitable aqueous phase can be used in the present processes and systems. For example, the aqueous phase can comprise water or a water-based buffer, e.g., PBS.

Any suitable multi-inlet vortexing reactor can be used in the present processes and systems. For example, the multi-inlet vortexing reactor can comprise a reaction chamber and multiple tangentially arranged inlets, through which the material for forming a nanoparticle in an organic solvent and/or an aqueous phase are injected into the reaction chamber. In another example, the multi-inlet vortexing reactor can comprise a cylindrical reaction (mixing) chamber where the multiple inlets meet. The multi-inlet vortexing reactor can comprise any suitable number of tangentially arranged inlets, through which the material for forming a nanoparticle in an organic solvent and/or an aqueous phase are injected into the reaction chamber. For example, the multi-inlet vortexing reactor can comprise 2, 3, 4, 5, 6, 7, 8, 9, 10, 15, 20, 25, 30, 35, 40, 45, 50 or more tangentially arranged inlets, through which the material for forming a nanoparticle in an organic solvent and/or an aqueous phase are injected into the reaction chamber.

The organic solvent phase can have any suitable flow rate. For example, the organic solvent phase can have a flow rate ranging from about 1 mL/minute to about 1,000 mL/minute, e.g., 1 mL/minute, 2 mL/minute, 3 mL/minute, 4 mL/minute, 5 mL/minute, 6 mL/minute, 7 mL/minute, 8 mL/minute, 9 mL/minute, 10 mL/minute, 15 mL/minute, 20 mL/minute, 25 mL/minute, 30 mL/minute, 35 mL/minute, 40 mL/minute, 45 mL/minute, 50 mL/minute, 60 mL/minute, 70 mL/minute, 80 mL/minute, 90 mL/minute, 100 mL/minute, 200 mL/minute, 300 mL/minute, 400 mL/minute, 500 mL/minute, 600 mL/minute, 700 mL/minute, 800 mL/minute, 900 mL/minute, or 1,000 mL/minute, or any sub-range within about 1 mL/minute to about 1,000 mL/minute, e.g., any range between any two of the above flow rates. In another example, the organic solvent phase can have a flow rate at or more than 1 L/minute, e.g., 1 L/minute, 2 L/minute, 3 L/minute, 4 L/minute, 5 L/minute, 6 L/minute, 7 L/minute, 8 L/minute, 9 L/minute, 10 L/minute, 50 L/minute, 100 L/minute, 500 L/minute, or 1,000 L/minute, or any sub-range within about 1 L/minute to about 1,000 L/minute, e.g., any range between any two of the above flow rates.

The aqueous phase can have any suitable flow rate. For example, the aqueous phase can have a flow rate ranging from about 1 mL/minute to about 1,000 mL/minute, e.g., 1 mL/minute, 2 mL/minute, 3 mL/minute, 4 mL/minute, 5 mL/minute, 6 mL/minute, 7 mL/minute, 8 mL/minute, 9 mL/minute, 10 mL/minute, 15 mL/minute, 20 mL/minute, 25 mL/minute, 30 mL/minute, 35 mL/minute, 40 mL/minute, 45 mL/minute, 50 mL/minute, 60 mL/minute, 70 mL/minute, 80 mL/minute, 90 mL/minute, 100 mL/minute, 200 mL/minute, 300 mL/minute, 400 mL/minute, 500 mL/minute, 600 mL/minute, 700 mL/minute, 800 mL/minute, 900 mL/minute, or 1,000 mL/minute, or any sub-range within about 1 mL/minute to about 1,000 mL/minute, e.g., any range between any two of the above flow rates. In another example, the aqueous phase can have a flow rate at or more than 1 L/minute, e.g., 1 L/minute, 2 L/minute, 3 L/minute, 4 mL/minute, 5 L/minute, 6 L/minute, 7 L/minute, 8 L/minute, 9 L/minute, 10 L/minute, 50 L/minute, 100 L/minute, 500 mL/minute, or 1,000 L/minute, or any sub-range within about 1 L/minute to about 1,000 L/minute, e.g., any range between any two of the above flow rates.

The present process can be conducted and the present system can be used at any suitable temperature. For example, the present process can be conducted and the present system can be used at a temperature ranging from about 0° C. to ambient temperature, e.g., about 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 25° C., 30° C., 35° C., or 40° C., or any sub-range within about 0° C. to ambient temperature, e.g., any range between any two of the above temperatures. In one embodiment, the present process can be conducted and the present system can be used at an ambient temperature.

The nanoparticle can have any suitable hydrodynamic size or diameter. For example, the nanoparticle can have a hydrodynamic size or diameter from about 10 nm to about 10 µm, e.g., about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, and 10 µm, or any sub-range within about 10 nm to about 10 µm, e.g., any range between any two of the above sizes.

The nanoparticle can have any suitable polydispersity index (PDI). For example, the nanoparticle can have a polydispersity index (PDI) from about 0.1 to about 0.7, e.g., 0.1, 0.2, 0.3, 0.4, 0.5, 0.6, or 0.7, or any sub-range within about 0.1 to about 0.7 PDI, e.g., any range between any two of the above PDI.

The nanoparticle can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

The TFF can be conducted using any suitable TFF system. For example, the TFF can be conducted using a TFF system that comprises a feed reservoir, a filter device and a collection device, the feed reservoir is in fluid communication with the filter device via an inlet on the filter device, the filter device is in fluid communication with the collection device via a permeate outlet on the filter device, and the filter device is in fluid communication with the feed reservoir via a retentate outlet on the filter device. Any suitable filter device can be used. For example, the filter device can be in a form of a cartridge, a cassette, or a column containing hollow a fiber filter. The filter device can comprise a filtration membrane having any suitable pore size. For example, the filter device comprises a filtration membrane having a pore size ranging from about 1 nm to about 500 nm, e.g., about 1 nm, 2 nm, 3 nm, 4 nm, 5 nm, 6 nm, 7 nm, 8 nm, 9 nm, 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, or any sub-range within about 1 nm to about 500 nm, e.g., any range between any two of the above sizes.

The TFF can be conducted using any suitable diafiltration process, e.g., a continuous, discontinuous, or sequential diafiltration process. The TFF can be conducted via any suitable number of cycles of diafiltration processes. For example, the TFF can be conducted via multiple cycles of diafiltration processes, e.g., multiple cycles of continuous diafiltration processes.

The nanoparticle can be collected via any suitable outlet on the filter device. For example, the nanoparticle can be collected via a retentate outlet on the filter device.

The TFF can be conducted using any suitable feeding rate. For example, the TFF can be conducted using a feeding rate ranging from about 0.1 mL/minute to about 1,000 mL/minute, e.g., 0.1 mL/minute, 0.2 mL/minute, 0.3 mL/minute, 0.4 mL/minute, 0.5 mL/minute, 0.6 mL/minute, 0.7 mL/minute, 0.8 mL/minute, 0.9 mL/minute, 1 mL/minute, 2 mL/minute, 3 mL/minute, 4 mL/minute, 5 mL/minute, 6 mL/minute, 7 mL/minute, 8 mL/minute, 9 mL/minute, 10 mL/minute, 15 mL/minute, 20 mL/minute, 25 mL/minute, 30 mL/minute, 35 mL/minute, 40 mL/minute, 45 mL/minute, 50 mL/minute, 60 mL/minute, 70 mL/minute, 80 mL/minute, 90 mL/minute, 100 mL/minute, 200 mL/minute, 300 mL/minute, 400 mL/minute, 500 mL/minute, 600 mL/minute, 700 mL/minute, 800 mL/minute, 900 mL/minute, or 1,000 mL/minute, or any sub-range within about 0.1 mL/minute to about 1,000 mL/minute, e.g., any range between any two of the above feeding rates.

The TFF can be conducted using any suitable feeding pressure. For example, the TFF can be conducted using a feeding pressure ranging from about 0.1 psi to about 100 psi, e.g., about 0.1 psi, 0.5 psi, 1 psi, 2 psi, 3 psi, 4 psi, 5 psi, 6 psi, 7 psi, 8 psi, 9 psi, 10 psi, 20 psi, 30 psi, 40 psi, 50 psi, 60 psi, 70 psi, 80 psi, 90 psi, 100 psi, or any sub-range within about 0.1 psi to about 100 psi, e.g., any range between any two of the above feeding pressures. The TFF can be conducted using any suitable retentate pressure. For example, the TFF can be conducted using a retentate pressure ranging from about 0.1 psi to about 100 psi, e.g., about 0.1 psi, 0.5 psi, 1 psi, 2 psi, 3 psi, 4 psi, 5 psi, 6 psi, 7 psi, 8 psi, 9 psi, 10 psi, 20 psi, 30 psi, 40 psi, 50 psi, 60 psi, 70 psi, 80 psi, 90 psi, 100 psi, or any sub-range within about 0.1 psi to about 100 psi, e.g., any range between any two of the above retentate pressures.

The TFF can be conducted using any suitable timeframe. For example, the TFF can be conducted within a time ranging from about 10 minutes to about 10 hours for one production batch, e.g., about 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, or any sub-range within about IO minutes to about IO hours, e.g., any range between any two of the above time points.

In one embodiment, the TFF can be used to reduce the amount of the organic solvent from the composition. In other embodiment, the TFF can be used to remove the organic solvent from the composition. For example, the TFF can be used to remove from about 50% to about 99.9999% of the organic solvent from the composition, e.g., about 50%, 60%, 70%, 80%, 90%, 91%, 92%, 93%, 94%, 95%, 96%, 97%, 98%, 99%, 99.9%, 99.99%, 99.999%, 99.9999%, or any sub-range within about 50% to about 99.9999%, e.g., any range between any two of the above purities with regard to the organic solvent. In still other embodiment, the TFF can be used to concentrate and/or enrich the nanoparticle about 1 fold to about 100 folds, e.g., about 1 fold, 2 folds, 3 folds, 4 folds, 5 folds, 6 folds, 7 folds, 8 folds, 9 folds, 10 folds, 20 folds, 30 folds, 40 folds, 50 folds, 60 folds, 70 folds, 80 folds, 90 folds, 100 folds, or any sub-range within about 1 fold to about 100 folds, e.g., any range between any two of the above concentrate and/or enrich fold(s) with regard to the nanoparticle.

The present process and system can be used to prepare the nanoparticle at any suitable production rate. For example, the present process and system can be used to prepare the nanoparticle at a production rate ranging from about 0.1 g/hour to about 1,000 g/hour for one production batch, e.g., 0.1 g/hr, 0.5 g/hr, 1 g/hr, 5 g/hr, 10 g/hr, 20 g/hr, 30 g/hr, 40 g/hr, 50 g/hr, 60 g/hr, 70 g/hr, 80 g/hr, 90 g/hr, 100 g/hr, 200 g/hr, 300 g/hr, 400 g/hr, 500 g/hr, 600 g/hr, 700 g/hr, 800 g/hr, 900 g/hr, 1,000 g/hr, or any sub-range within about 0.1 g/hr to about 1,000 g/hr, e.g., any range between any two of the above production rates.

In some embodiments, a part or the whole process can be conducted under aseptic conditions, e.g., in a clean room.

A nanoparticle prepared by the above process and system is also provided.

The nanoparticle prepared by the above process and system can be used for any suitable purposes or applications. For example, the nanoparticle prepared by the above process and system can be used for any suitable research, prognostic, diagnostic and/or therapeutic applications, with or without carrying a prognostic, diagnostic and/or therapeutic agent. In another example, the nanoparticle prepared by the above process and system can be used as an intermediate for preparing a further modified nanoparticle. In some embodiments, the nanoparticle prepared by the above process and system can be used as a nanoparticle core for preparing a cellular or viral membrane coated nanoparticle, e.g., the cellular or viral membrane coated nanoparticle as described in Section D below.

C. Processes and Systems for Preparing a Cellular or Viral Membrane

In still another aspect, the present invention provides for a process for preparing a process for preparing a cellular or viral membrane, which process comprises: 1) lysing a cell, a cellular vesicle or a virus to obtain a composition comprising a cellular or viral membrane and a non-membrane cellular or viral moiety; and 2) subjecting said composition to tangential flow filtration (TFF) to separate said cellular or viral membrane from said non-membrane cellular or viral moiety.

The cell, cellular vesicle or virus can be lysed using any suitable methods. For example, the cell, cellular vesicle or virus can be lysed using a hypotonic treatment, sonication, shear force (French press), or a nitrogen decompression chamber.

A cell or a cellular vesicle can be lysed to obtain a composition comprising a cellular membrane and a non-membrane cellular moiety. The cell or cellular vesicle can be derived from any suitable organism. For example, the cell or cellular vesicle can be derived from a unicellular organism (e.g. a bacterium or fungus) or a multicellular organism (e.g., a plant, an animal, a non-human mammal, vertebrate, or a human).

In some embodiments, the cell or cellular vesicle can be derived from a multicellular organism such as a vertebrate, a non-human mammal or a human. In other embodiments, the cell or cellular vesicle can be derived from a blood cell, e.g. a red blood cell, a white blood cell or a platelet. In still other embodiments, the cell or cellular vesicle can be derived from an immune cell (e.g., macrophage, monocyte, B-cell, or T-cell), a tumor or cancer cell, and other cells, such as an epithelial cell, an endothelial cell, or a neural cell. In yet other embodiments, the cell or cellular vesicle can be derived from a non-terminally differentiated cell, such as a stem cell, including a hematopoietic stem cell, a bone marrow stem cell, a mesenchymal stem cell, a cardiac stem cell, a neural stem cell. In yet other embodiments, the cell or cellular vesicle can be derived from a cell component or cell organelle including, but not limited to, an exosome, a secretory vesicle, a synaptic vesicle, an endoplasmic reticulum (ER), a Golgi apparatus, a mitochondrion, a vacuole or a nucleus.

The present process and system can be used to obtain any suitable cellular membrane. For example, the present process and system can be used to obtain a plasma membrane, an intracellular membrane, or a membrane of a cellular vesicle. In some embodiments, the present process and system can be used to obtain a plasma membrane derived from a blood cell, e.g., a red blood cell, a white blood cell or a platelet.

In some embodiments, a virus can be lysed to obtain a composition comprising a viral membrane and a non-membrane viral moiety.

In some embodiments, the non-membrane cellular or viral moiety to be separate by the present process and system can be a cellular organelle, a viral particle, a molecule or an aggregate or complex thereof. The cellular organelle to be separate by the present process and system can be a nuclei, a mitochondrion, a chloroplast, a ribosome, an ER, a Golgi apparatus, a lysosome, a proteasome, a secretory vesicle, a vacuole or a microsome. The molecule to be separate by the present process and system can be an inorganic molecule, an organic molecule and a complex thereof. Exemplary organic molecules include an amino acid, a peptide, a polypeptide, a protein, a nucleoside, a nucleotide, an oligonucleotide, a polynucleotide, a nucleic acid, a vitamin, a monosaccharide, an oligosaccharide, a carbohydrate, a lipid and a complex thereof.

The TFF can be conducted using any suitable TFF system. For example, the TFF can be conducted using a TFF system that comprises a feed reservoir, a filter device and a collection device, the feed reservoir is in fluid communication with the filter device via an inlet on the filter device, the filter device is in fluid communication with the collection device via a permeate outlet on the filter device, and the filter device is in fluid communication with the feed reservoir via a retentate outlet on the filter device. Any suitable filter device can be used. For example, the filter device can be in a form of a cartridge, a cassette, or a column containing hollow a fiber filter. The filter device can comprise a filtration membrane having any suitable pore size. For example, the filter device comprises a filtration membrane having a pore size ranging from about 1 nm to about 500 nm, e.g., about 1 nm, 2 nm, 3 nm, 4 nm, 5 nm, 6 nm, 7 nm, 8 nm, 9 nm, 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, or any sub-range within about 1 nm to about 500 nm, e.g., any range between any two of the above sizes.

The TFF can be conducted using any suitable diafiltration process, e.g., a continuous, discontinuous, or sequential diafiltration process. The TFF can be conducted via any suitable number of cycles of diafiltration processes. For example, the TFF can be conducted via multiple cycles of diafiltration processes, e.g., multiple cycles of continuous diafiltration processes.

The cellular or viral membrane can be collected via any suitable outlet on the filter device. For example, the cellular or viral membrane can be collected via a retentate outlet on the filter device.

The TFF can be conducted using any suitable feeding rate. For example, the TFF can be conducted using a feeding rate ranging from about 0.1 mL/minute to about 1,000 mL/minute, e.g., 0.1 mL/minute, 0.2 mL/minute, 0.3 mL/minute, 0.4 mL/minute, 0.5 mL/minute, 0.6 mL/minute, 0.7 mL/minute, 0.8 mL/minute, 0.9 mL/minute, 1 mL/minute, 2 mL/minute, 3 mL/minute, 4 mL/minute, 5 mL/minute, 6 mL/minute, 7 mL/minute, 8 mL/minute, 9 mL/minute, 10 mL/minute, 15 mL/minute, 20 mL/minute, 25 mL/minute, 30 mL/minute, 35 mL/minute, 40 mL/minute, 45 mL/minute, 50 mL/minute, 60 mL/minute, 70 mL/minute, 80 mL/minute, 90 mL/minute, 100 mL/minute, 200 mL/minute, 300 mL/minute, 400 mL/minute, 500 mL/minute, 600 mL/minute, 700 mL/minute, 800 mL/minute, 900 mL/minute, or 1,000 mL/minute, or any sub-range within about 0.1 mL/minute to about 1,000 mL/minute, e.g., any range between any two of the above feeding rates.

The TFF can be conducted using any suitable feeding pressure. For example, the TFF can be conducted using a feeding pressure ranging from about 0.1 psi to about 100 psi, e.g., about 0.1 psi, 0.5 psi, 1 psi, 2 psi, 3 psi, 4 psi, 5 psi, 6 psi, 7 psi, 8 psi, 9 psi, 10 psi, 20 psi, 30 psi, 40 psi, 50 psi, 60 psi, 70 psi, 80 psi, 90 psi, 100 psi, or any sub-range within about 0.1 psi to about 100 psi, e.g., any range between any two of the above feeding pressures. The TFF can be conducted using any suitable retentate pressure. For example, the TFF can be conducted using a retentate pressure ranging from about 0.1 psi to about 100 psi, e.g., about 0.1 psi, 0.5 psi, 1 psi, 2 psi, 3 psi, 4 psi, 5 psi, 6 psi, 7 psi, 8 psi, 9 psi, 10 psi, 20 psi, 30 psi, 40 psi, 50 psi, 60 psi, 70 psi, 80 psi, 90 psi, 100 psi, or any sub-range within about 0.1 psi to about 100 psi, e.g., any range between any two of the above retentate pressures.

The TFF can be conducted using any suitable timeframe. For example, the TFF can be conducted within a time ranging from about 10 minutes to about 10 hours for one production batch, e.g., about 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, or any sub-range within about 10 minutes to about 10 hours, e.g., any range between any two of the above time points.

In some embodiments, the TFF can be used to reduce the amount of the non-membrane cellular or viral moiety and/or an organic solvent. In other embodiments, the TFF can be used to remove the non-membrane cellular or viral moiety and/or an organic solvent. For example, the TFF can be used to remove from about 50% to about 99.9999% of the non-membrane cellular or viral moiety and/or an organic solvent, e.g., about 50%, 60%, 70%, 80%, 90%, 91%, 92%, 93%, 94%, 95%, 96%, 97%, 98%, 99%, 99.9%, 99.99%, 99.999%, 99.9999%, or any sub-range within about 50% to about 99.9999%, e.g., any range between any two of the above purities with regard to the non-membrane cellular or viral moiety and/or an organic solvent. In still other embodiments, the TFF can be used to concentrate and/or enrich the cellular or viral membrane for from about 1 fold to about 100 folds, e.g., about 1 fold, 2 folds, 3 folds, 4 folds, 5 folds, 6 folds, 7 folds, 8 folds, 9 folds, 10 folds, 20 folds, 30 folds, 40 folds, 50 folds, 60 folds, 70 folds, 80 folds, 90 folds, 100 folds, or any sub-range within about 1 fold to about 100 folds, e.g., any range between any two of the above concentrate and/or enrich fold(s) with regard to the cellular or viral membrane.

The present process and system can be used to prepare the cellular or viral membrane at any suitable production rate. For example, the present process and system can be used to prepare the cellular or viral membrane at a production rate ranging from about 1 g (measured as protein content)/hour to about 5 kg (measured as protein content)/hour for one production batch, e.g., 1 g (measured as protein content)/hour, 2 g (measured as protein content)/hour, 3 g (measured as protein content)/hour, 4 g (measured as protein content)/hour, or 5 g (measured as protein content)/hour, 6 g (measured as protein content)/hour, 7 g (measured as protein content)/hour, 8 g (measured as protein content)/hour, 9 g (measured as protein content)/hour, or 10 g (measured as protein content)/hour, 20 g (measured as protein content)/hour, 30 g (measured as protein content)/hour, 40 g (measured as protein content)/hour, 50 g (measured as protein content)/hour, 60 g (measured as protein content)/hour, 70 g (measured as protein content)/hour, 80 g (measured as protein content)/hour, 90 g (measured as protein content)/hour, 100 g (measured as protein content)/hour, 200 g (measured as protein content)/hour, 300 g (measured as protein content)/hour, 400 g (measured as protein content)/hour, 500 g (measured as protein content)/hour, 600 g (measured as protein content)/hour, 700 g (measured as protein content)/hour, 800 g (measured as protein content)/hour, 900 g (measured as protein content)/hour, 1 kg (measured as protein content)/hour, 2 kg (measured as protein content)/hour, 3 kg (measured as protein content)/hour, 4 kg (measured as protein content)/hour, 5 kg (measured as protein content)/hour, or any sub-range within about 1 g (measured as protein content)/hour to about 5 kg (measured as protein content)/hour, e.g., any range between any two of the above production rates.

In some embodiments, the present process and system can be used to prepare the cellular membrane derived from a blood cell, e.g., a red blood cell. In other embodiments, the present process and system can also be used to separate the red blood cellular membrane from a non-membrane cellular moiety derived from a red blood cell. The present process and system can also be used to separate the red blood cellular membrane from any suitable non-membrane cellular moiety. In some embodiments, the non-membrane cellular moiety to be separated by the present process and system can be a protein derived from a red blood cell, e.g., hemoglobin.

In some embodiments, the TFF can be used to remove any suitable level of a red blood cell protein, e.g., hemoglobin. For example, the TFF can be used to remove from about 50% to about 99.9999% of a red blood cell protein, e.g., hemoglobin. In some embodiments, the TFF can be used to remove about 50%, 60%, 70%, 80%, 90%, 91%, 92%, 93%, 94%, 95%, 96%, 97%, 98%, 99%, 99.9%, 99.99%, 99.999%, 99.9999%, or any sub-range within about 50% to about 99.9999%, e.g., any range between any two of the above purities with regard to the red blood cell protein, e.g., hemoglobin.

In other embodiments, the TFF can be used to concentrate and/or enrich the red blood cellular membrane to any suitable level or degree. For example, the TFF can be used to concentrate and/or enrich the red blood cellular membrane from about 1 fold to about 100 folds, e.g., about 1 fold, 2 folds, 3 folds, 4 folds, 5 folds, 6 folds, 7 folds, 8 folds, 9 folds, 10 folds, 20 folds, 30 folds, 40 folds, 50 folds, 60 folds, 70 folds, 80 folds, 90 folds, 100 folds, or any sub-range within about 1 fold to about 100 folds, e.g., any range between any two of the above concentrate and/or enrich fold(s) with regard to the red blood cellular membrane.

The present process and system can be used to prepare the red blood cellular membrane at any suitable production rate. For example, the present process and system can be used to prepare the red blood cellular membrane at a production rate ranging from 1 g (measured as protein content)/hour to about 5 kg (measured as protein content)/hour for one production batch, e.g., 1 g (measured as protein content)/hour, 2 g (measured as protein content)/hour, 3 g (measured as protein content)/hour, 4 g (measured as protein content)/hour, or 5 g (measured as protein content)/hour, 6 g (measured as protein content)/hour, 7 g (measured as protein content)/hour, 8 g (measured as protein content)/hour, 9 g (measured as protein content)/hour, or 10 g (measured as protein content)/hour, 20 g (measured as protein content)/hour, 30 g (measured as protein content)/hour, 40 g (measured as protein content)/hour, 50 g (measured as protein content)/hour, 60 g (measured as protein content)/hour, 70 g (measured as protein content)/hour, 80 g (measured as protein content)/hour, 90 g (measured as protein content)/hour, 100 g (measured as protein content)/hour, 200 g (measured as protein content)/hour, 300 g (measured as protein content)/hour, 400 g (measured as protein content)/hour, 500 g (measured as protein content)/hour, 600 g (measured as protein content)/hour, 700 g (measured as protein content)/hour, 800 g (measured as protein content)/hour, 900 g (measured as protein content)/hour, 1 kg (measured as protein content)/hour, 2 kg (measured as protein content)/hour, 3 kg (measured as protein content)/hour, 4 kg (measured as protein content)/hour, 5 kg (measured as protein content)/hour, or any sub-range within about 1 g (measured as protein content)/hour to about 5 kg (measured as protein content)/hour, e.g., any range between any two of the above production rates.

The present process and system can further comprise assessing, or a means for assessing, a property of the cellular or viral membrane. The property of the cellular or viral membrane to be assessed can be a biological, chemical and/or physical property. In some embodiments, the present process and system can further comprise assessing, or a means for assessing, a property of the red blood cellular membrane. The property of the red blood cellular membrane to be assessed can be a biological, chemical and/or physical property, e.g., acetylcholinesterase activity, hemoglobin content, phospholipid content and/or total protein content of the red blood cellular membrane.

In some embodiments, a part or the whole process can be conducted under aseptic conditions, e.g., in a clean room.

A cellular or viral membrane prepared by the above process and system is also provided. In some embodiments, a red blood cellular membrane prepared by the above process and system is also provided.

The cellular or viral membrane prepared by the above process and system can be used for any suitable purposes or applications. For example, the cellular or viral membrane prepared by the above process and system can be used for any suitable research, prognostic, diagnostic and/or therapeutic applications. In another example, the cellular or viral membrane prepared by the above process and system can be used as an intermediate for preparing a cellular or viral membrane coated nanoparticle, e.g., the cellular or viral membrane coated nanoparticle as described in Section D below.

D. Processes and Systems for Preparing a Cellular or Viral Membrane Coated Nanoparticle In yet another aspect, the present invention provides for a process for preparing a cellular or viral membrane coated nanoparticle, which process comprises mixing a nanoparticle inner core comprising a non-cellular material with a cellular membrane derived from a cell or a membrane derived from a virus using a high shear fluid processor to form a nanoparticle comprising said inner core and an outer surface comprising said cellular membrane or viral membrane.

In yet another aspect, the present invention provides for a system for preparing a cellular or viral membrane coated nanoparticle, which system comprises: 1) a system for preparing a nanoparticle core, which system comprises: a) a multi-inlet vortexing reactor that is configured to mix a material for forming a nanoparticle core in an organic solvent and an aqueous phase to form a composition comprising said nanoparticle core; and b) a tangential flow filtration (TFF) system that is configured to reduce the amount of or to remove said organic solvent from said composition; 2) a system for preparing a cellular or viral membrane, which system comprises: a) means for lysing a cell, a cellular vesicle or a virus to obtain a composition comprising a cellular or viral membrane and a non-membrane cellular or viral moiety; and b) a tangential flow filtration (TFF) system that is configured to separate said cellular or viral membrane from said non-membrane cellular or viral moiety; and 3) a high shear fluid processor that is configured to mix said nanoparticle inner core comprising said material with said cellular membrane derived from a cell or a membrane derived from a virus to form a nanoparticle comprising said inner core and an outer surface comprising said cellular membrane or viral membrane.

The inner core of the nanoparticle can comprise any suitable material. For example, the material can comprise a polymer. In one embodiment, the polymer can be a hydrophobic polymer that coils when switched from an organic solvent to an aqueous phase, e.g., water. In another embodiment, the inner core of the nanoparticle can comprise a biocompatible or a synthetic material, such as poly(lactic-co-glycolic acid) (PLGA), polylactic acid (PLA), polyglycolic acid (PGA), polycaprolactone (PCL), polylysine, or polyglutamic acid. In one preferred embodiment, the polymer is poly(lactic-c-glycolic acid) (PLGA). In other embodiments, the inner core of the nanoparticle supports the outer surface.

The nanoparticle can comprise any suitable cellular membrane derived from a cell or a cellular source, e.g., a red blood cell. For example, the nanoparticle can comprise a plasma membrane or an intracellular membrane derived from a cell, e.g., a red blood cell. In some embodiments, the cellular membrane comprises a plasma membrane derived from a red blood cell, e.g., a plasma membrane derived from a human red blood cell. In some embodiments, the nanoparticle can comprise any suitable naturally occurring cellular membrane derived from a cell, e.g., a red blood cell. In some embodiments, the cellular membrane comprises a naturally occurring plasma membrane derived from a red blood cell, e.g., a naturally occurring plasma membrane derived from a human red blood cell.

In some embodiments, the cellular membrane can be derived from a unicellular organism (e.g. a bacterium or fungus) or a multicellular organism (e.g., a plant, an animal, a non-human mammal, vertebrate, or a human). In other embodiments, the cellular membrane can be derived from a blood cell, e.g. a red blood cell, a white blood cell or a platelet. In still other embodiments, the cellular membrane can be derived from an immune cell (e.g., macrophage, monocyte, B-cell, or T-cell), a tumor or cancer cell, and other cells, such as an epithelial cell, an endothelial cell, or a neural cell. In yet other embodiments, the cellular membrane can be derived from a non-terminally differentiated cell, such as a stem cell, including a hematopoietic stem cell, a bone marrow stem cell, a mesenchymal stem cell, a cardiac stem cell, a neural stem cell. In yet other embodiments, the cellular membrane can be derived from a cell component or cell organelle including, but not limited to, an exosome, a secretory vesicle, a synaptic vesicle, an endoplasmic reticulum (ER), a Golgi apparatus, a mitochondrion, a vacuole or a nucleus.

The present nanoparticle can further comprise a releasable cargo. The nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the subject or by a change of a physical parameter surrounding the nanoparticle. The nanoparticle can comprise any suitable types of releasable cargo. For example, the releasable cargo can be a therapeutic agent, a prophylactic agent, a diagnostic or marker agent, a prognostic agent, or a combination thereof. The therapeutic agent can be a cytotoxic drug capable of cell killing. Any suitable cytotoxic drugs can be used. For example, cytotoxic drugs can be an anthracycline, e.g., doxorubicin or daunorubicin, a taxane, e.g., docetaxel or paclitaxel, or an immunosuppressive agent, e.g., methotrexate or cyclosporin A. In another example, the releasable cargo can be a metallic particle, a polymeric particle, a dendrimer particle, or an inorganic particle or the releasable cargo can be in the form of a metallic particle, a polymeric particle, a dendrimer particle, or an inorganic particle.

The nanoparticle can have any suitable size. For example, the nanoparticle can have a diameter from about 10 nm to about 10 μm. In certain embodiments, the diameter of the nanoparticle is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 μm, 2 μm, 3 μm, 4 μm, 5 μm, 6 μm, 7 μm, 8 μm, 9 μm, and 10 μm, or any sub-range within about 10 nm to about 10 μm, e.g., any range between any two of the above sizes.

The nanoparticle can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the nanoparticle substantially lacks constituents of the cell or virus, e.g., red blood cell, from which the cellular or viral membrane is derived. For example, the nanoparticle can lack about 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the cell or virus, e.g., red blood cell, from which the cellular or viral membrane is derived. In some embodiments, the nanoparticle comprises a plasma membrane derived from a red blood cell and the nanoparticle substantially lacks hemoglobin. For example, the nanoparticle can lack about 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the hemoglobin.

In some embodiments, the nanoparticle substantially maintains natural structural integrity or activity of the cellular or viral membrane or the constituents of the cellular or viral membrane. For example, the nanoparticle can retain about 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity. In some embodiments, the nanoparticle substantially maintains natural structural integrity of the cellular or viral membrane or the constituents of the cellular or viral membrane including primary, secondary, tertiary and/or quaternary structure of the cellular membrane, the membrane derived from a virus or the constituents of the cellular membrane or viral membrane. In some embodiments, the nanoparticle substantially maintains activity of the cellular or viral membrane or the constituents of the cellular or viral membrane including binding activity, receptor activity and/or enzymatic activity of the cellular membrane, the membrane derived from a virus or the constituents of the cellular membrane or viral membrane.

In some embodiments, the nanoparticle is biocompatible or biodegradable. For example, the inner core of the nanoparticle comprises PLGA and the outer surface of the nanoparticle comprises a plasma membrane derived from a cell, e.g., a red blood cell.

The nanoparticle can have any suitable half-life in vivo. For example, the nanoparticle can have a half-life in blood circulation in vivo for at least about 2-5 times of the half-life of a PEG-coated, comparable nanoparticle, or has a half-life in blood circulation in vivo for at least about 1 to about 40 hours.

In some embodiments, the nanoparticle substantially lacks immunogenicity to a subject, a mammal, a non-human mammal or a human, to which the nanoparticle is configured to administer. For example, the cellular membrane can be derived from a cell, e.g., a red blood cell, from the same species of the subject. In another example, the subject is a human and the cellular membrane is derived from a human cell, e.g., a human red blood cell. In some embodiments, the cellular membrane can be derived from a cell, e.g., a red blood cell, of the subject to be treated. For example, the cellular membrane can be derived from a red blood cell of the human to be treated.

The outer surface of the nanoparticle can comprise a hybrid membrane comprising a cellular membrane derived from a cell or virus and a synthetic membrane. In some embodiments, the outer surface of the nanoparticle can comprise a hybrid membrane comprising at least about 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w) of a cellular or viral membrane. In other embodiments, the outer surface of the nanoparticle can comprise a hybrid membrane comprising at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w) of a synthetic membrane. For example, the outer surface of the nanoparticle can comprise a hybrid membrane comprising about 5-10% (w/w) of a cellular or viral membrane and about 95-99% (w/w) of a synthetic membrane, about 11-25% (w/w) of a cellular or viral membrane and about 75-89% (w/w) of a synthetic membrane, about 50% (w/w) of a cellular or viral membrane and about 50% (w/w) of a synthetic membrane, about 51-75% (w/w) of a cellular or viral membrane and about 49-25% (w/w) of a synthetic membrane, or about 90-99% (w/w) of a cellular or viral membrane and about 1-10% (w/w) of a synthetic membrane.

In some embodiments, the nanoparticle inner core can be prepared by a process descried in Section B above. In some embodiments, the cellular membrane derived from a cell or the membrane derived from a virus can be prepared by a process descried in Section C above.

In some embodiments, the high shear fluid processor can be configured to generate shear force in mixing a nanoparticle inner core comprising a non-cellular material with a cellular membrane derived from a cell or a membrane derived from a virus. In other embodiments, the high shear fluid processor can be configured to generate impact force in mixing a nanoparticle inner core comprising a non-cellular material with a cellular membrane derived from a cell or a membrane derived from a virus. In still other embodiments, the high shear fluid processor can be configured to generate shear force and impact force in mixing a nanoparticle inner core comprising a non-cellular material with a cellular membrane derived from a cell or a membrane derived from a virus.

Any suitable high shear fluid processor can be used. For example, the high shear fluid processor can comprise a microchannel and the high shear fluid processor can be configured to generate an average velocity that is up to about 500 meter/second (mis) in the microchannel, e.g., about 1 m/s, 10 m/s, 50 m/s, 100 m/s, 150 m/s, 200 m/s, 250 m/s, 300 m/s, 350 m/s, 400 m/s, 450 m/s, or 500 m/s, or any sub-range within about 1 m/s to about 500 m/s, e.g., any range between any two of the above average velocities, in the microchannel. The high shear fluid processor can also be configured to generate an average shear rate of up to about 4,000,000 inverse second ($SEC^{-1}$), e.g., about 1,000 $SEC^{-1}$, 10,000 $SEC^{-1}$, 100,000 $SEC^{-1}$, 200,000 $SEC^{-1}$, 300,000 $SEC^{-1}$, 400,000 $SEC^{-1}$, 500,000 $SEC^{-1}$, 600,000 $SEC^{-1}$, 700,000 $SEC^{-1}$, 800,000 $SEC^{-1}$, 900,000 $SEC^{-1}$, 1,000,000 $SEC^{-1}$, 2,000,000 $SEC^{-1}$, 3,000,000 $SEC^{-1}$, or 4,000,000 $SEC^{-1}$, or any sub-range within about 1,000 $SEC^{-1}$ to about 4,000,000 $SEC^{-1}$, e.g., any range between any two of the above average shear rates.

The high shear fluid processor can be a microfluidizer (or a microfluidizer processor) or a homogenizer that generates high shear force. In some embodiments, the microfluidizer can be configured to generate a substantially constant pressure from about 200 psi to about 10,000 psi, e.g., about 200 psi, 300 psi, about 400 psi, 500 psi, about 600 psi, 700 psi, about 800 psi, 900 psi, about 1,000 psi, 2,000 psi, 3,000 psi, 4,000 psi, 5,000 psi, 6,000 psi, 7000 psi, 8,000 psi, 9,000 psi, 10,000 psi, or higher pressure, or any sub-range within from about 200 psi to about 10,000, e.g., any range between any two of the above substantially constant pressures.

In other embodiments, the microfluidizer can be configured to generate a substantially uniform shear rate of up to about $10^7$ $SEC^{-1}$, e.g., about $10^5$ $SEC^{-1}$, $10^6$ $SEC^{-1}$, $2\times10^6$ $SEC^{-1}$, $3\times10^6$ $SEC^{-1}$, $4\times10^6$ $SEC^{-1}$, $5\times10^6$ $SEC^{-1}$, $6\times10^6$ $SEC^{-1}$, $7\times10^6$ $SEC^{-1}$, $8\times10^6$ $SEC^{-1}$, $9\times10^6$ $SEC^{-1}$, $10^7$ $SEC^{-1}$, or any sub-range within from about $10^5$ $SEC^{-1}$ to about $10^7$ $SEC^{-1}$, e.g., any range between any two of the above substantially uniform shear rates.

The microfluidizer can have any suitable configuration. In some embodiments, the microfluidizer has the microfluidics reaction technology (MRT) configuration that comprises, from upstream to downstream, an inlet for inputting a nanoparticle inner core comprising a non-cellular material and/or a cellular membrane derived from a cell or a membrane derived from a virus, an intensifier pump for generating a static pressure, an impinging jet chamber for generating a high shear pressure on a mixture of the nanoparticle inner core and the cellular or viral membrane to form a cellular or viral membrane coated nanoparticle, and an outlet for outputting the cellular or viral membrane coated nanoparticle. In other embodiments, the microfluidizer comprises a Z-type of interaction chamber. In still other embodiments, the microfluidizer comprises a Y-type of interaction chamber.

The present process and system can be used to prepare the cellular or viral membrane coated nanoparticle at any suitable production rate. For example, the present process and system can be used to prepare the cellular or viral membrane coated nanoparticle at a production rate ranging from about 0.1 g/hour to about 1,500 g/hour for one production batch, e.g., about 0.1 g/hr, 0.5 g/hr, 1 g/hr, 5 g/hr, 10 g/hr, 20 g/hr, 30 g/hr, 40 g/hr, 50 g/hr, 60 g/hr, 70 g/hr, 80 g/hr, 90 g/hr, 100 g/hr, 200 g/hr, 300 g/hr, 400 g/hr, 500 g/hr, 600 g/hr, 700 g/hr, 800 g/hr, 900 g/hr, 1,000 g/hr, 1,100 g/hr, 1,200 g/hr, 1,300 g/hr, 1,400 g/hr, 1,500 g/hr, or any sub-range within about 0.1 g/hr to about 1,500 g/hr, e.g., any range between any two of the above production rates.

The present process can further comprise assessing, and the present system can further comprise a means for assessing, a property of the cellular or viral membrane coated nanoparticle. The property of the cellular or viral membrane coated nanoparticle to be assessed can be a biological, chemical and/or physical property. For example, the present process can further comprise assessing, and the present system can further comprise a means for assessing, a property of a red blood cellular membrane coated nanoparticle. Any suitable property of a red blood cellular membrane coated nanoparticle can be assessed. For example, acetylcholinesterase activity, hemoglobin content, phospholipid content and/or total protein content of the red blood cellular membrane coated nanoparticle can be assessed.

In some embodiments, a part or the whole process can be conducted under aseptic conditions, e.g., in a clean room.

A cellular or viral membrane coated nanoparticle prepared by the above process and system is provided. In some embodiments, a red blood cellular membrane coated nanoparticle prepared by the above process and system is also provided.

A medicament delivery system, which comprises an effective amount of the nanoparticle prepared by the above process and system, is provided. In some embodiments, the medicament delivery system further comprises another active ingredient, and/or a medically and/or pharmaceutically acceptable carrier or excipient.

A pharmaceutical composition, which comprises an effective amount of the nanoparticle prepared by the above process and system and a pharmaceutically acceptable carrier or excipient, is provided. In some embodiments, the pharmaceutical composition further comprises another active ingredient.

A method for treating and/or preventing a disease or condition in a subject is provided. The method comprises administering, to a subject in need of such treatment and/or prevention, an effective amount of the nanoparticle prepared by the above process and system, a medicament delivery system that comprises an effective amount of the nanoparticle prepared by the above process and system, or a pharmaceutical composition that comprises an effective amount of the nanoparticle prepared by the above process and system.

The present method can be used for any suitable purposes or applications. For example, the present method can be used for treating and/or preventing a disease or condition that is selected from the group consisting of an infectious disease, a parasitic disease, a neoplasm, a cancer, a disease of the blood and blood-forming organs, a disorder involving the immune mechanism, endocrine, nutritional and metabolic diseases, a mental and behavioral disorder, a disease of the nervous system, a disease of the eye and adnexam, a disease of the ear and mastoid process, a disease of the circulatory system, a disease of the respiratory system, a disease of the digestive system, a disease of the skin and subcutaneous tissue, a disease of the musculoskeletal system and connective tissue, a disease of the genitourinary system, pregnancy, childbirth and the puerperium, a condition originating in the perinatal period, a congenital malformation, a deformation, a chromosomal abnormality, an injury, a poisoning, a consequence of external causes, and an external cause of morbidity and mortality.

The present method can be used on any suitable subject. For example, the present method can be used for treating and/or preventing a disease or condition on a human, a non-human mammal, a non-human animal, e.g., a vertebrate.

The present method can use any suitable nanoparticle prepared by the above process and system. For example, the present method can use a nanoparticle wherein the cellular membrane in the nanoparticle is derived from a cell of the same species of the subject to be treated or is derived from a cell of the subject to be treated. In another example, the present method can use a nanoparticle wherein the cellular membrane in the nanoparticle is derived from a red blood cell of the same species of the subject to be treated and the red blood cell has the same blood type of the subject to be treated.

The present method can further comprise administering another active ingredient to the subject and/or a pharmaceutically acceptable carrier or excipient to the subject. The present method can further comprise administering the nanoparticle via a medicament delivery system.

The nanoparticle can be administered via any suitable route. For example, the nanoparticle can be administered via an oral, nasal, inhalational, parental, intravenous, intraperitoneal, subcutaneous, intramuscular, intradermal, topical, or rectal route. The nanoparticle can be administered to any suitable target site. For example, the nanoparticle can be administered to a specific type of cell, tissue, organ or system, or a specific location in the subject, e.g., a target dermal site, blood, etc.

Use of an effective amount of a nanoparticle prepared by the above process and system for the manufacture of a medicament for treating and/or preventing a disease or condition in a subject is also provided.

E. Pharmaceutical Compositions and Administration Routes

The pharmaceutical compositions comprising the nanoparticles, alone or in combination with other active ingredient(s), described herein may further comprise one or more pharmaceutically-acceptable excipients. A pharmaceutically-acceptable excipient is a substance that is non-toxic and otherwise biologically suitable for administration to a subject. Such excipients facilitate administration of the nanoparticles, alone or in combination with other active ingredient(s), described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the various embodiments are sterile compositions. Pharmaceutical compositions may be prepared using compounding techniques known or that become available to those skilled in the art.

Sterile compositions are within the present disclosure, including compositions that are in accord with national and local regulations governing such compositions.

The pharmaceutical compositions and the nanoparticles, alone or in combination with other active ingredient(s), described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. The nanoparticles, alone or in combination with other active ingredient(s), described herein, and preferably in the form of a pharmaceutical composition, may be administered by a suitable route of delivery, such as oral, parenteral, rectal, nasal, topical, or ocular routes, or by inhalation. In some embodiments, the compositions are formulated for intravenous or oral administration.

For oral administration, the nanoparticles, alone or in combination with another active ingredient, may be provided in a solid form, such as a tablet or capsule, or as a solution, emulsion, or suspension. To prepare the oral compositions, the nanoparticles, alone or in combination with other active ingredient(s), may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinylpyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compositions may be formulated for rectal administration as a suppository. For parenteral use, including intravenous, intramuscular, intraperitoneal, intranasal, or subcutaneous routes, the nanoparticles, alone or in combination with other active ingredient(s), may be provided in sterile aqueous solutions or suspensions, buffered to an appropriate pH and isotonicity or in parenterally acceptable oil. Suitable aqueous vehicles can include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000

µg/kg/minute of agent admixed with a pharmaceutical carrier over a period ranging from several minutes to several days.

For nasal, inhaled, or oral administration, the nanoparticles, alone or in combination with other active ingredient(s), may be administered using, for example, a spray formulation also containing a suitable carrier.

For topical applications, the nanoparticles, alone or in combination with other active ingredient(s), are preferably formulated as creams or ointments or a similar vehicle suitable for topical administration. For topical administration, the nanoparticles, alone or in combination with other active ingredient(s), may be mixed with a pharmaceutical carrier at a concentration of about 0.1% to about 10% of drug to vehicle. Another mode of administering the nanoparticles, alone or in combination with other active ingredient(s), may utilize a patch formulation to effect transdermal delivery.

In certain embodiments, the present disclosure provides pharmaceutical composition comprising the nanoparticles, alone or in combination with other active ingredient(s), and methylcellulose. In certain embodiments, methylcellulose is in a suspension of about 0.1, 0.2, 0.3, 0.4, or 0.5 to about 1%. In certain embodiments, methylcellulose is in a suspension of about 0.1 to about 0.5, 0.6, 0.7, 0.8, 0.9, or 1%. In certain embodiments, methylcellulose is in a suspension of about 0.1 to about 1%. In certain embodiments, methylcellulose is in a suspension of about 0.1, 0.2, 0.3, 0.4, 0.5, 0.6, 0.7, 0.8, 0.8, or 1%. In certain embodiments, methylcellulose is in a suspension of about 0.5%.

As used herein, "preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition.

One of ordinary skill in the art may modify the formulations within the teachings of the specification to provide numerous formulations for a particular route of administration. In particular, the nanoparticles, alone or in combination with other active ingredient(s), may be modified to render them more soluble in water or other vehicle. It is also well within the ordinary skill of the art to modify the route of administration and dosage regimen of a particular nanoparticle, alone or in combination with other active ingredient(s), in order to manage the pharmacokinetics of the present compounds for maximum beneficial effect in a patient.

F. Example—Manufacturing of Red Blood Cell Membrane-Coated Nanoparticles Introduction In an exemplary embodiment, a large-scale nanosponge production, with a primary aim to develop Good Manufacturing Practice (GMP)-compatible processes to facilitate the platform's clinical translation, is developed. The overall design emphasizes both scalability and GMP-compatibility. Specifically, multi-inlet vortex technology is developed to enable a continuous and high-throughput nanoparticle self-assembly process that otherwise could only be used in small-scale production. In addition, unit operations are integrated with established GMP-compatibility into nanosponge production. Particularly, tangential flow filtration (TFF) and microfluidizer, two technologies with validated applications and Food and Drug Administration (FDA) conformity, are used to minimize downstream development risks. Notably, these technologies allow for direct scale-up, hence paving the way toward the pilot production for large volume applications.

Overview of an Exemplary Nanosponge Large-Scale Production Process

An exemplary nanosponge production process is divided into three major processes: (a) polymeric core preparation, (b) RBC membrane purification, and (c) core-membrane fusion (FIG. 1). Specifically, multi-inlet vortexing is used for core production, combined with TFF-enabled solvent exchange for purification and concentration. In the second process, membrane production is carried out with semi-automated hypotonic treatment, followed by TFF for purification. In the third process, microfluidizer is used to generate high shear force for membrane-core fusion. The overall process is modular, emphasizing not only the scalability and GMP-compatibility, but also the ability of integration for aseptic processing.

Polymeric Core Production Process

An exemplary process to produce polymeric cores is divided into two steps. In the first step, multi-inlet vortexing is used for continuous and high throughput core production. In the second step, TFF is used to exchange solvents for purification and concentration.

Figure 2A:
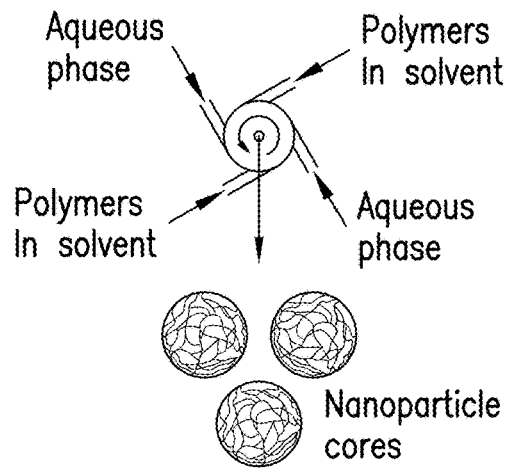
FIG. 2 illustrates an exemplary production for polymer cores. (A) Schematic working mechanism of the multi-inlet vortex reactor (MIVR) device. Polymers dissolved in organic solvent and aqueous phase are fed into a circular reaction chamber that facilitates nanoparticle self-assembly. The resulting nanoparticles are collected from the outlet. (B-C) Production of polymer cores with MIVR. During production, the flow rate of the organic phase is 4 mL/min, the flow rate of the water is 20 mL/min, and the polymer concentration is 1 mg/mL. The cores are characterized by their hydrodynamic size in (B) and polydispersity index (PDI) in (C). Results are from 4 independent batch runs.
Figure 2B:
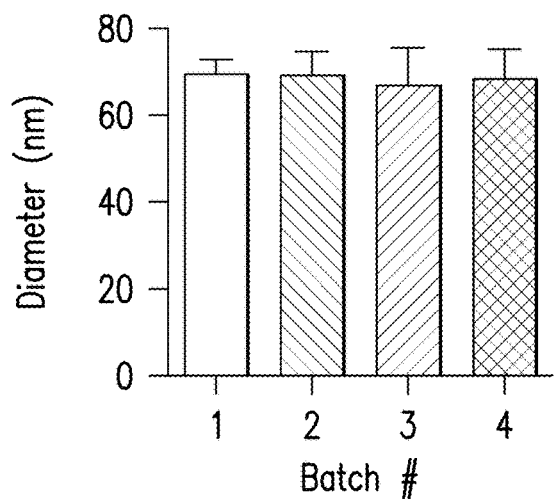
Figure 2C:
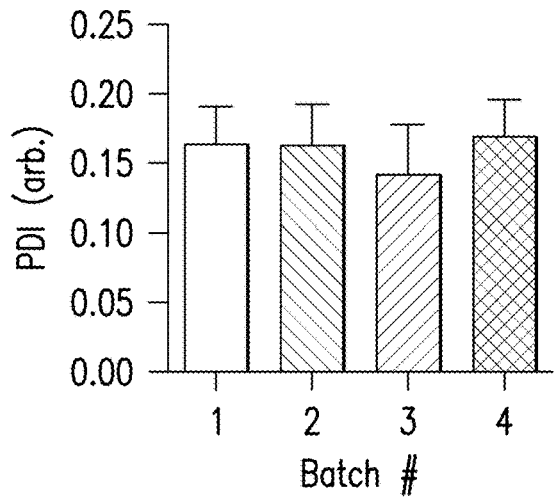

Core fabrication through multi-inlet mixing. To scale up the nanoparticle production, a multi-inlet vortex reactor is utilized to produce cores at large quantities. The design and structure of an exemplary multi-inlet vortexing reactor (MIVR) is illustrated in FIG. 2A. The reactor comprises a cylindrical reaction chamber and four tangentially arranged inlets, through which the reactants are injected into the chamber. At high flow rates, turbulence promotes continuous mixing of solvent and non-solvent to create high supersaturation to initialize particle precipitation. By using MIVR, the flow rate ratio of water and organic solvent (acetonitrile) was optimized. Under optimized conditions, it was able to produce polymeric cores with a diameter smaller than 100 nm and a polydispersity index of approximately 0.2 (FIGS. 2B and C).

Figure 3B:
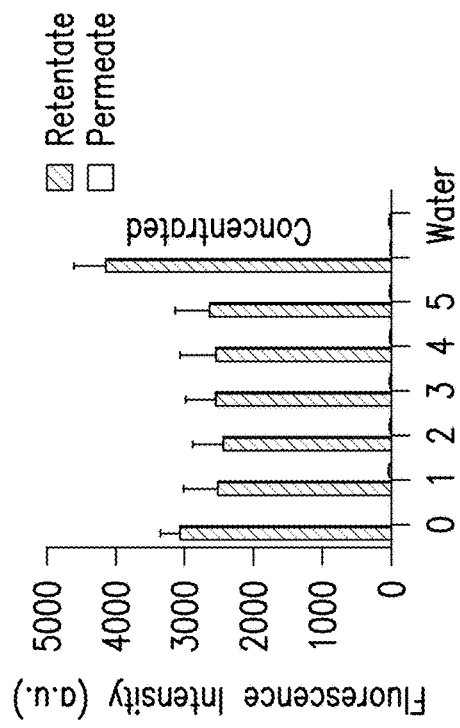
FIG. 3 illustrates an exemplary scale up of the polymeric nanoparticle (NP) cores purification process (buffer exchange) via a continuous tangential flow filtration (TFF) method and NP cores loss study was tested. (A) Size and (B) Fluorescence intensity of fluorescent dye loaded NP cores in retentate and permeate solutions after each round of diafiltration using TFF were measured. No NP cores or polymer loss was detected. (C) Time, feeding pressure and retentate pressure were determined at different feed rates when using 30 kD cutoff hollow-fiber filter in TFF stem.
Figure 3A:
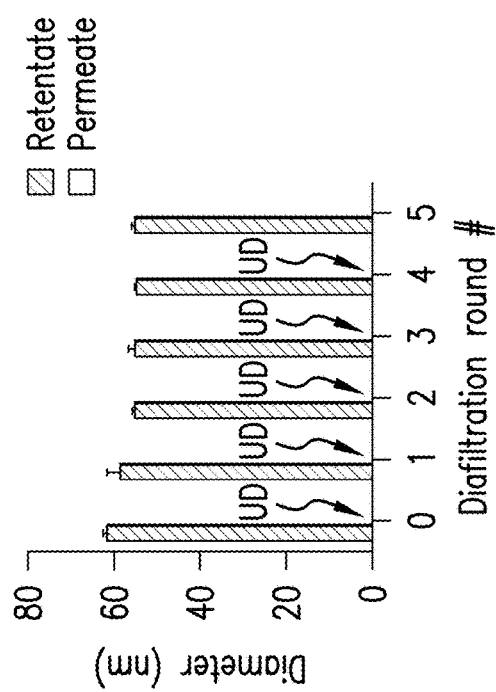
Figure 3C:
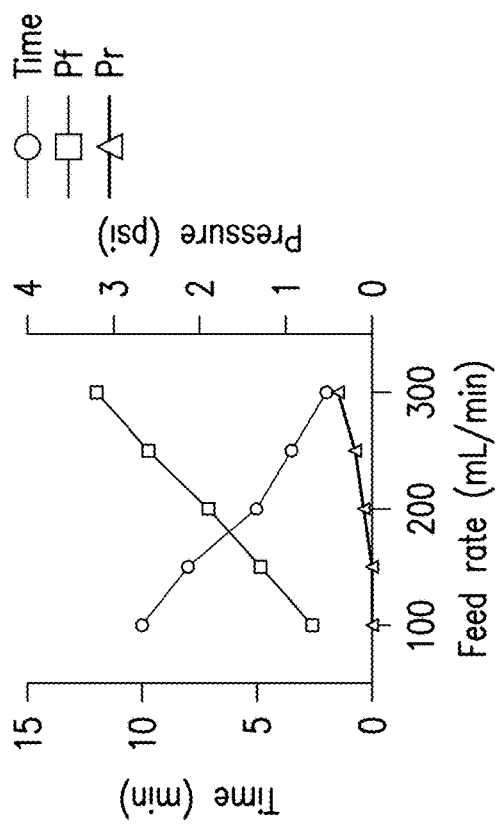
Figure 4A:
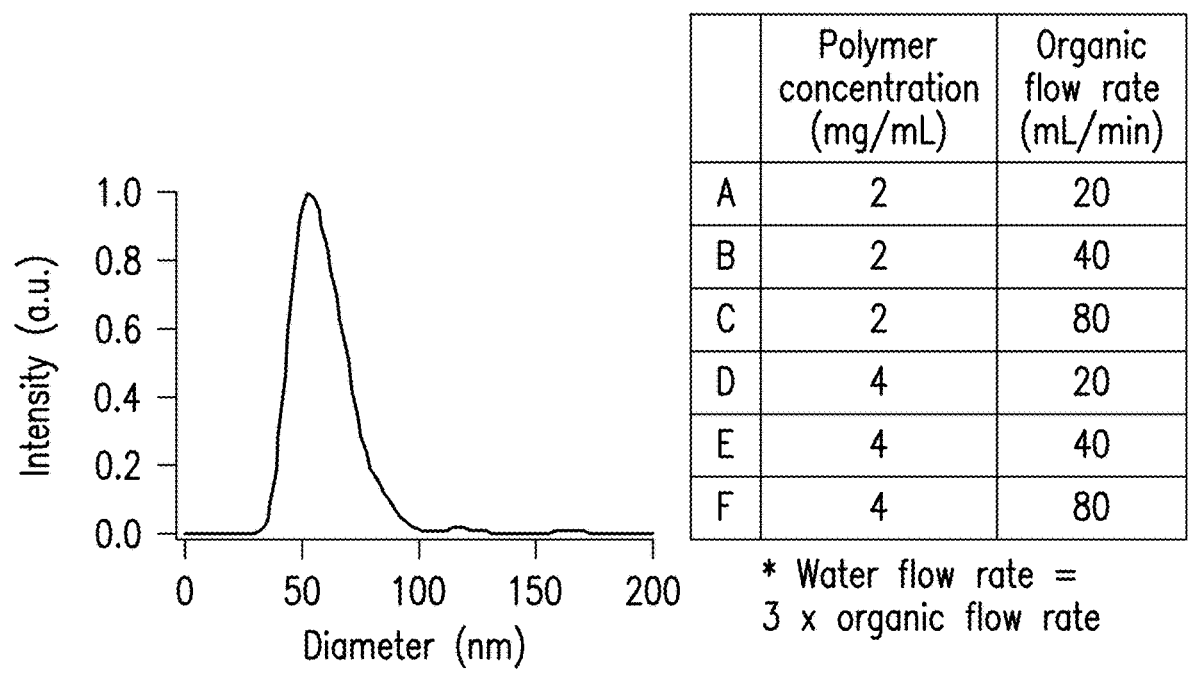
FIG. 4 illustrates an exemplary polymeric core produced after connecting MIVR with TFF. The hydrodynamic sizes are measured with NanoSight® NS500. When polymer concentration was kept at 2 mg/mL in acetonitrille, flow rate of acetonitrille at 40 mg/mL, and water flow rate at 120 mg/mL, the particle cores exhibited the smallest size and monodispersity.
Figure 4B:
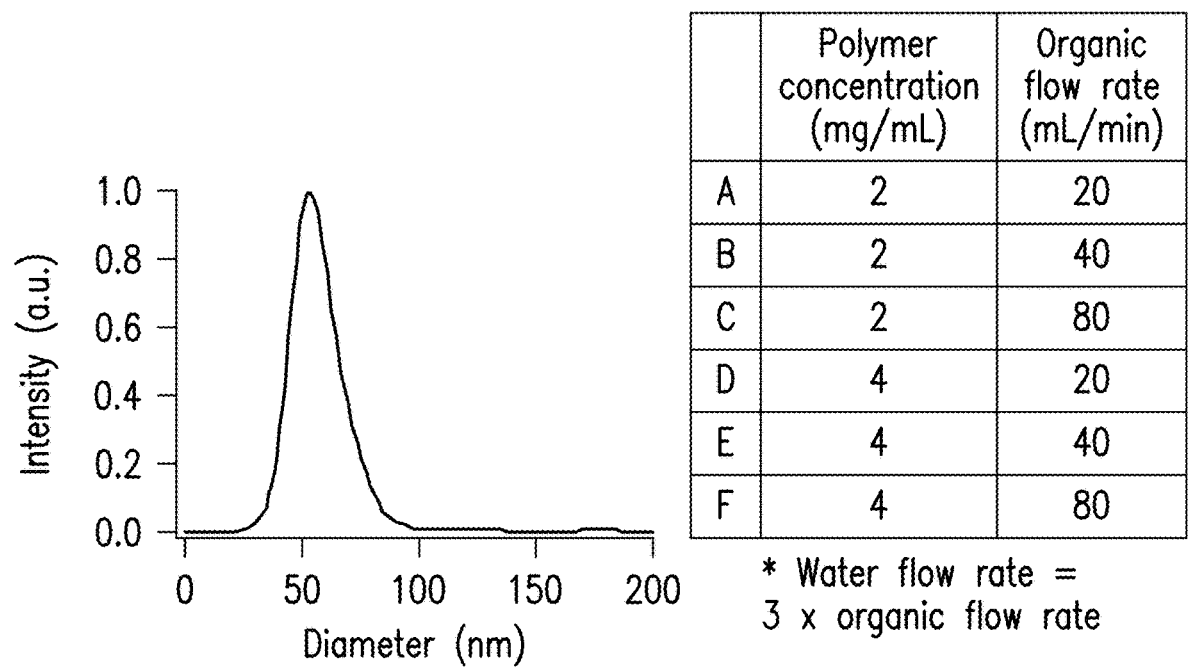
Figure 4C:
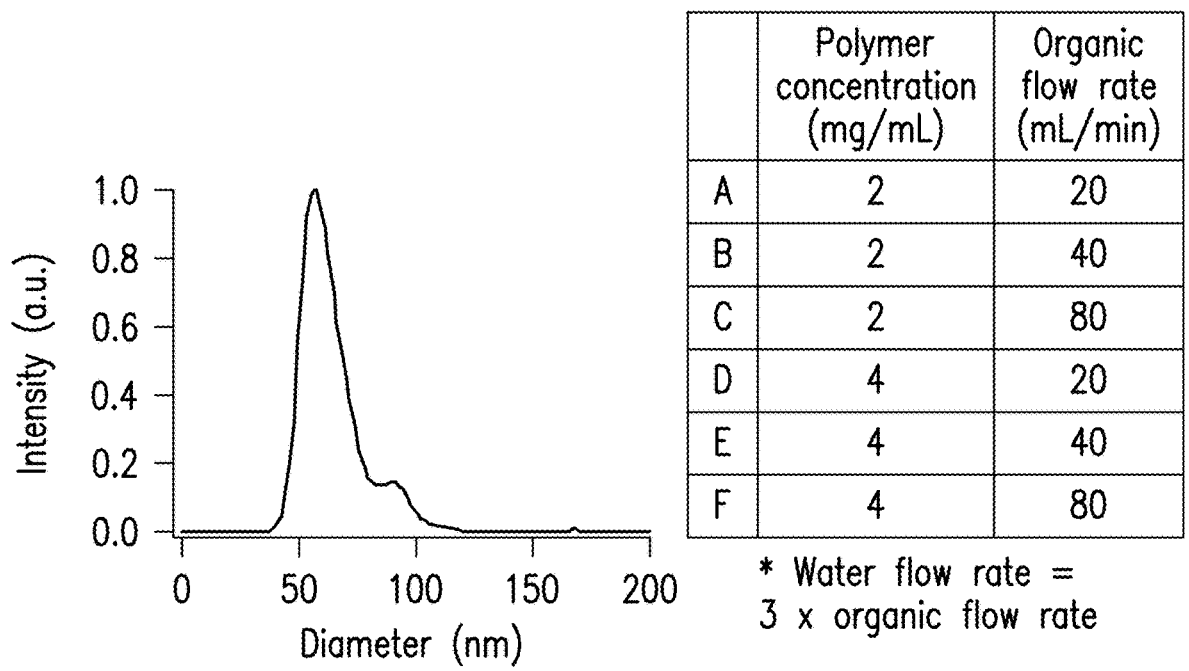
Figure 4D:
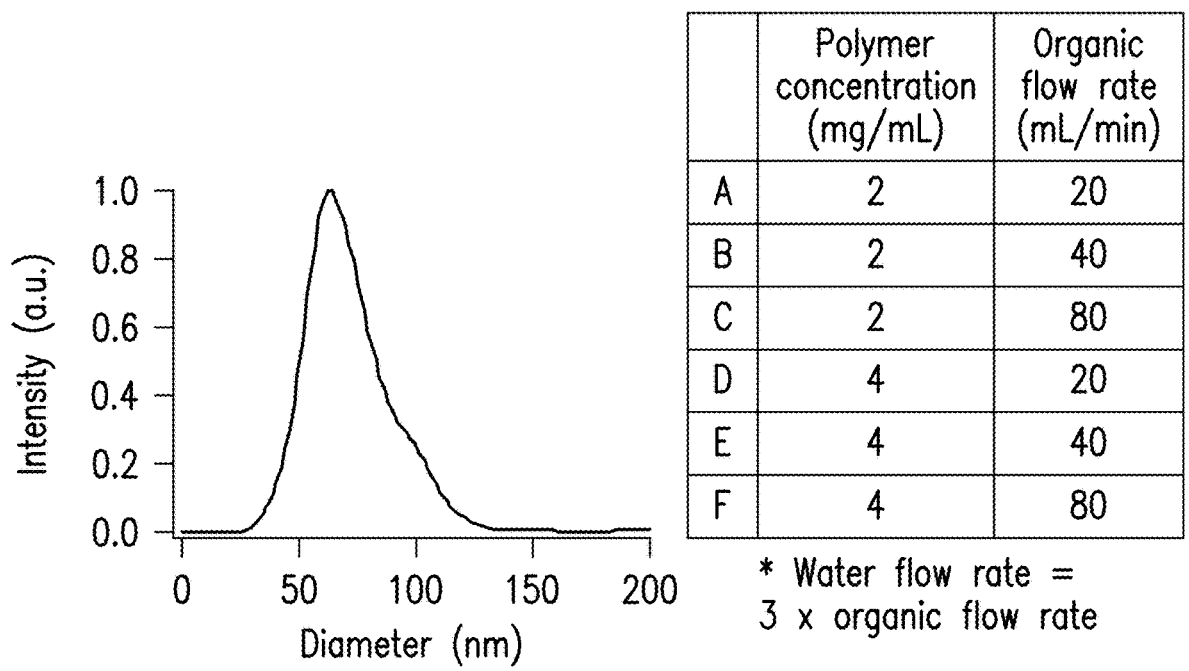
Figure 4E:
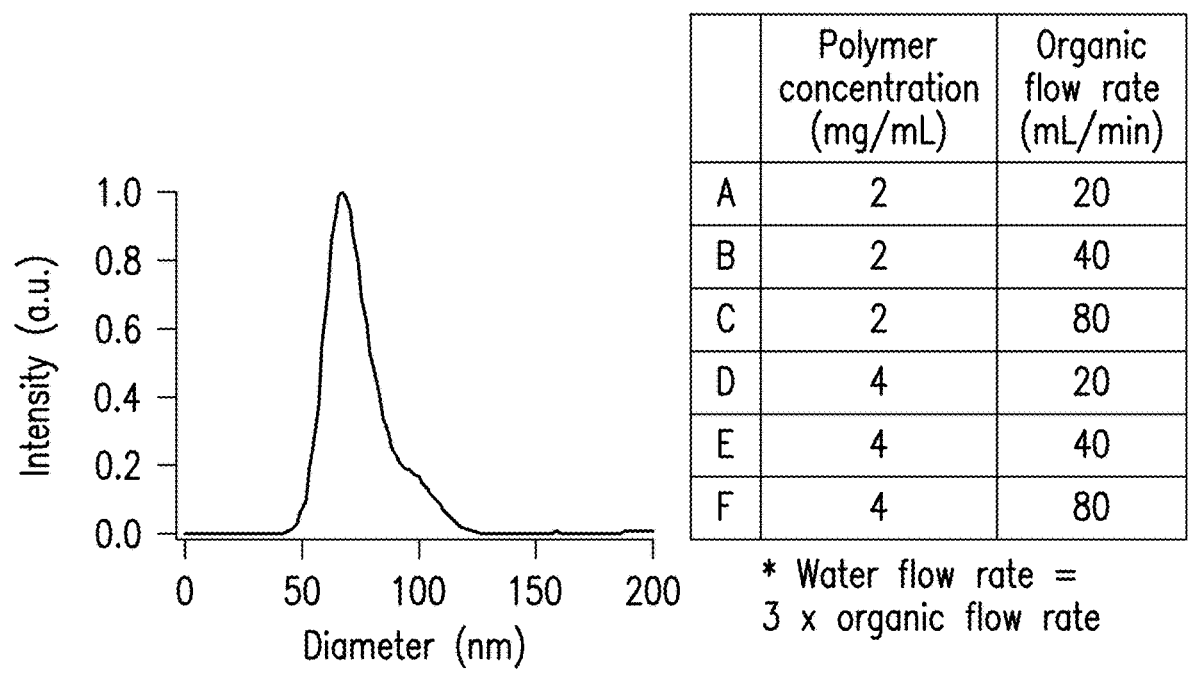
Figure 4F:
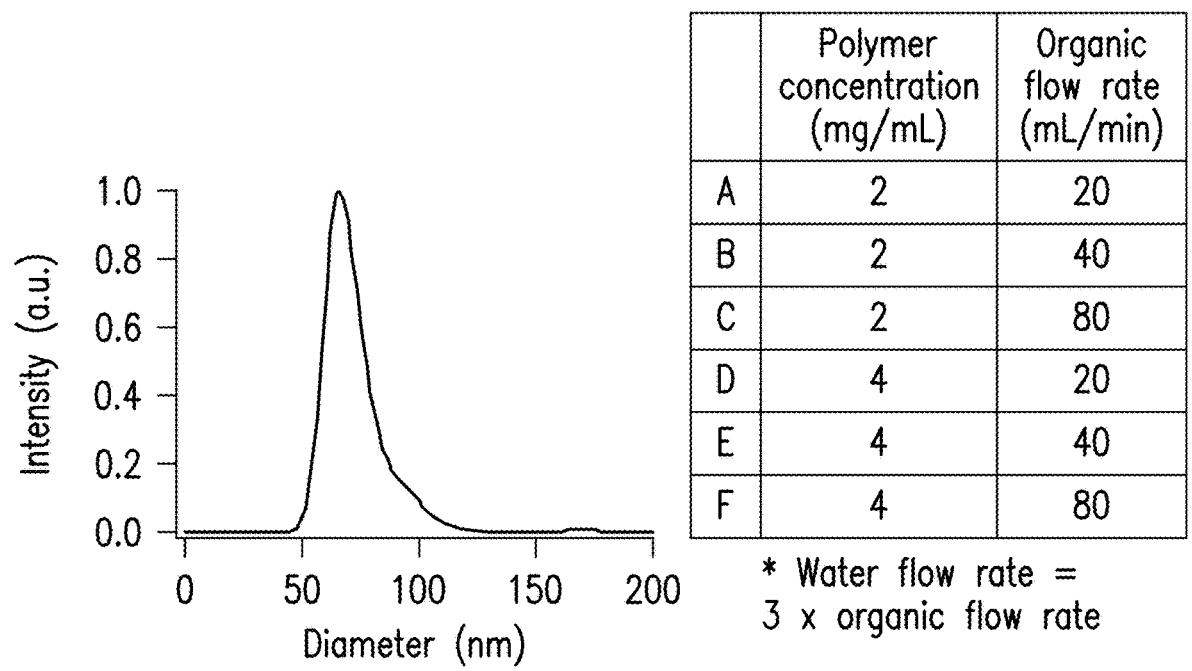

Solvent exchange through TFF. To remove the organic solvent, evaporation is commonly used in research. However, evaporation process is slow and prone to induce polymer film formation. Herein, a solvent exchange process using TFF is developed, which gradually removes acetonitrille, the organic solvent used to dissolve PLGA, from the solution. TFF allows for quantifying the amount of organic solvent removed. Compared to other methods, it also concentrates polymer cores during solvent exchange, hence minimizing the risk of sample loss and contamination. TFF columns were screened with different pore sizes and fiber diameters, and the parameters with the best performance were determined. Buffer exchange with five continuous diafiltrations resulted in greater than 99% acetonitrile removal. Particle cores remained stable during each diafiltration process: the core diameter showed negligible changes (FIG. 3A). To test the particle loss during the filtration, the cores were also labeled with fluorescent dyes and measured the fluorescence intensity of the retentate and permeate, respectively. As shown in FIG. 3B, no obvious particle loss was observed. Finally, linear correlations of feed rates with production parameters were observed, including processing time, feeding pressure, and retentate pressure, indicating that the buffer exchange process is scalable (FIG. 3C).

Continuous large-scale core production. Following the optimization of core production with MIVR and TFF-based buffer exchange, MIVR were connected with TFF and the large-scale core production (FIG. 4A-F) was tested. In this task, the pressure imbalance due to the large flow rate difference between acetonitrile and water was overcome by rearranging the feed streams. Cores with a predominant diameter of ~50 nm and a production rate ~5 g/hr can be manufactured.

Further adjustments. If the production rate needs to be increased, additional pump heads can be mounted without changing the current parameters. From the processing perspective, instead of adding additional pump heads, the polymer stock concentration can be increased and flow rates can be adjusted for core production. It is one objective to increase core production rate to above 10 g/hr. Both MIVR and TFF can be scaled up and/or adjusted to achieve this objective.

RBC Membrane Purification

Conventional method to produce purified RBC membranes uses a hypotonic treatment method in combination with ultracentrifugation to separate RBC membranes and intracellular proteins. For large-scale production, ultracentrifugation method is not cost effective. An alternative method is needed.

Figure 5A:
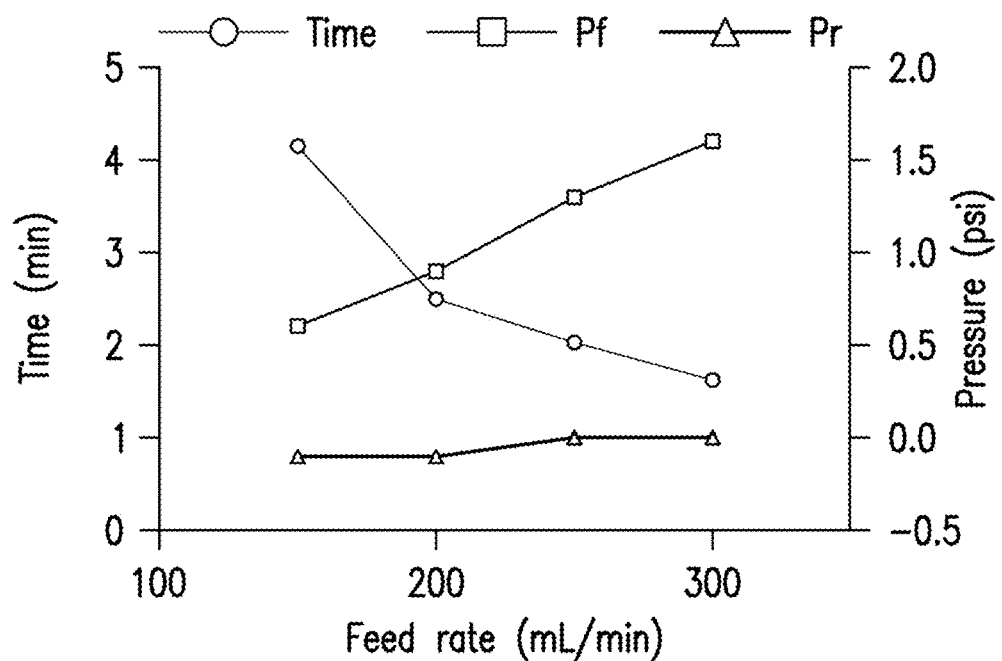
FIG. 5 illustrates an exemplary, scalable RBC membrane purification process via a continuous TFF method. (A) Time, feeding pressure and retentate pressure were measured at different feed rates when using hollow-fiber filter with 0.2 μm cutoff in TFF System. (B) Representative images of permeate solutions after each round of purification process. (C) Hemoglobin absorbance in permeate and membrane after each purification round.
Figure 5B:
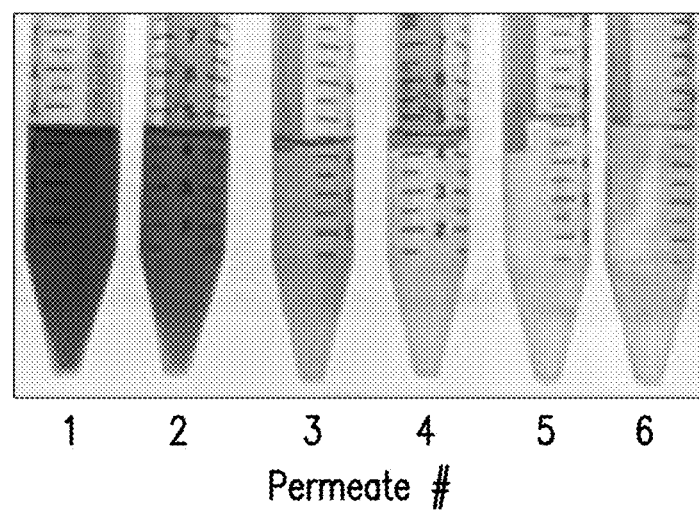
Figure 5C:
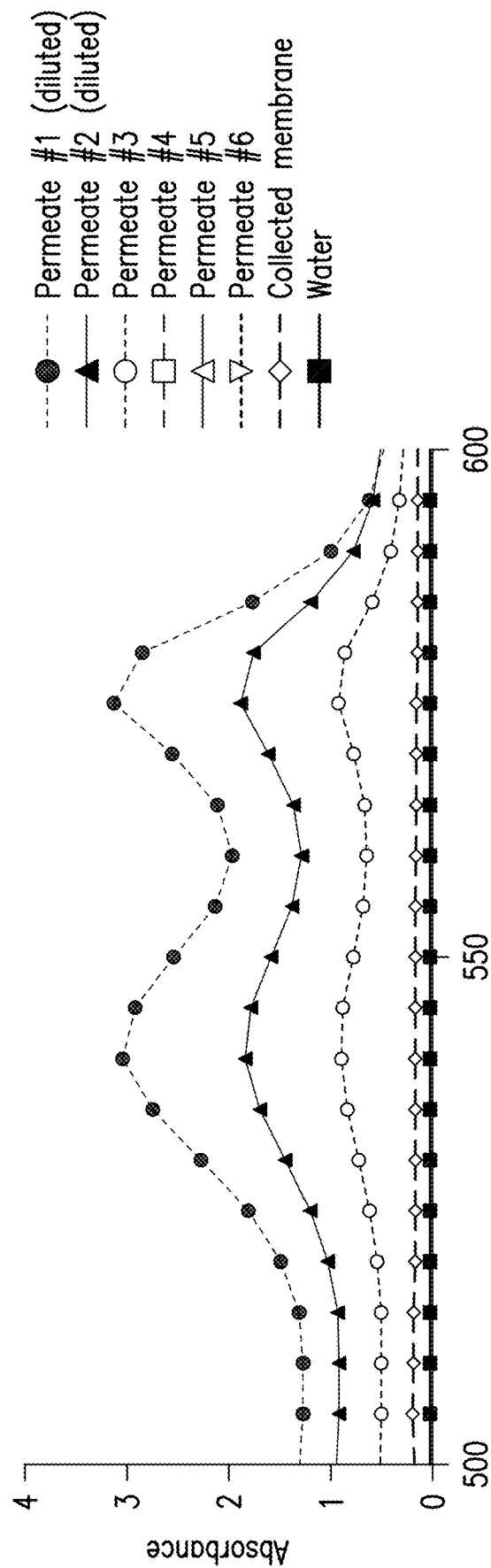

In this example, a scalable RBC membrane purification process via a continuous TFF method was explored. In the study, time, feeding pressure, and retentate pressure were measured at different feed rates when using hollow-fiber filter with 0.2 μm cutoff in A KrosFlo Research Iii TFF System. After RBCs were disrupted by using a hypotonic treatment method, TFF technique was employed to separate RBC membranes and intracellular proteins (primarily hemoglobin with a molecular weight of 64 kDa). Blood sample was treated with hypotonic buffer of 9 volume equivalent to disrupt RBC, followed by the TFF process to concentrate the volume to 1 volume equivalent and diafiltrate with 5 volumes equivalents (500 mL) of hypotonic buffer to remove released hemoglobin. Permeate (waste) solution was collected. This process was repeated 6 times. The waste solution collected from each round and the purified membrane solution were then measured for absorbance of hemoglobin as shown in FIG. 5.

Further adjustments. An exemplary panel of assays for characterizing RBC membranes are shown in Table 1. When combined, these assays quantify the chemical and biological properties of RBC membrane. The exemplary panel of assays is developed as part of quality assurance and quality control assays.

TABLE 1

Assays proposed for RBC membrane characterization

| Name of the Assay | Vendor | Catalog Number |
| --- | --- | --- |
| Acetylcholinesterase Activity | Sigma-Aldrich | MAK119-1KT |
| Hemoglobin content | Sigma-Aldrich | MAK115-1KT |
| Phospholipid content | Sigma-Aldrich | MAK122-1KT |
| Total protein content | Pierce Biosciences | 23235 |

Figure 6:
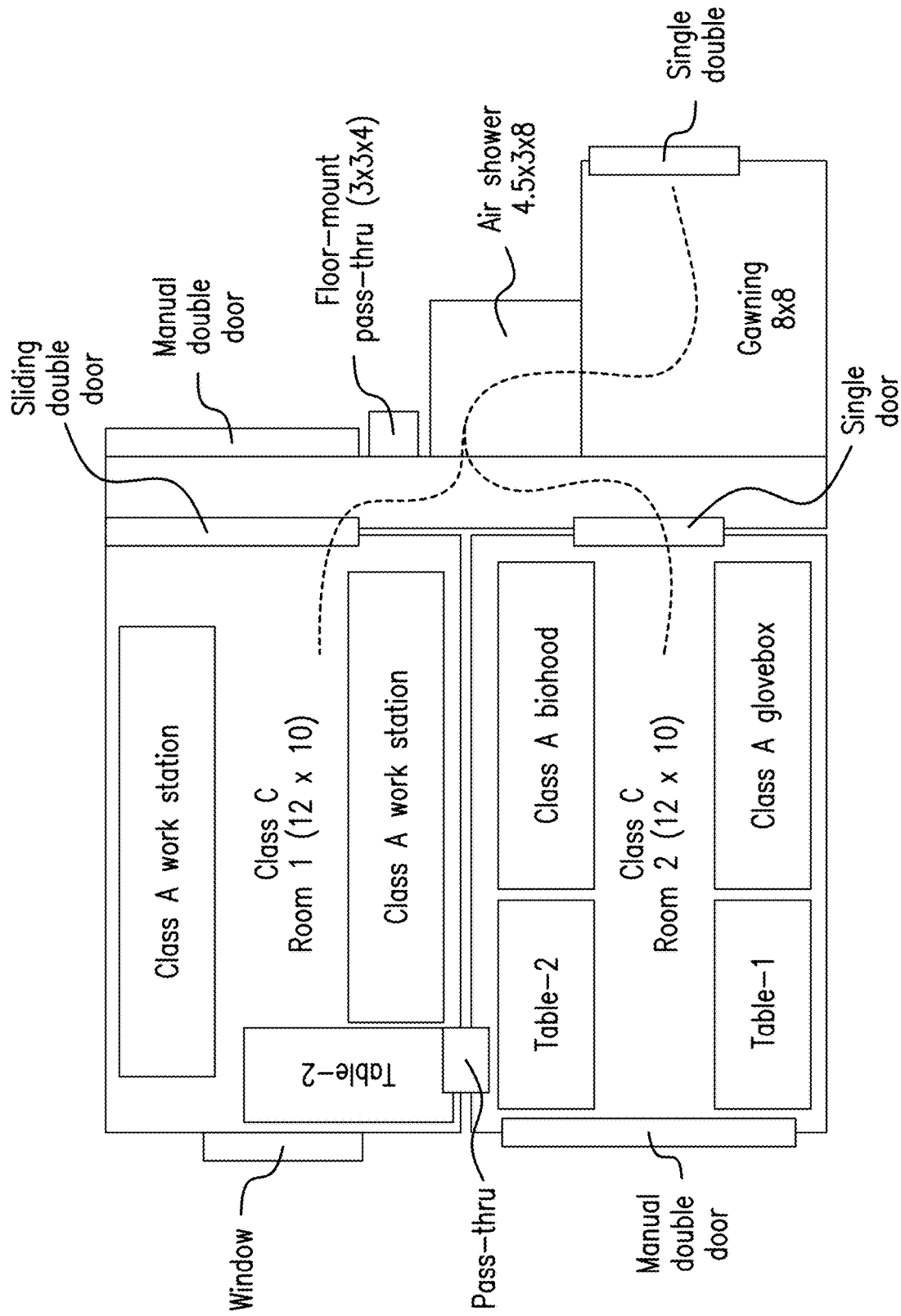
FIG. 6 illustrates an exemplary clean room layout. Two Class C (ISO 7) rooms will be used to house Class A (ISO 5) work stations for nanosponge manufacturing. The clean room is also equipped with gowning and air shower area.

Clean room construction. An exemplary clean room is shown in FIG. 6. The exemplary clean room has two separate operation rooms with ISO 7 classification (FIG. 6). Each room also houses workstations with ISO 5 classification, in which a part or whole process for preparing a nanoparticle, for preparing a cellular or viral membrane and/or for preparing a cellular or viral membrane coated nanoparticle can be conducted.

G. Further Exemplary Embodiments

Overview

In an exemplary embodiment, the nanosponge production is divided into three major processes: (a) polymeric core preparation, (b) RBC membrane purification, and (c) core-membrane fusion (FIG. 1). Specifically, multi-inlet vortexing is used for core production, combined with TFF-enabled solvent exchange for purification and concentration. In the second step, membrane production is carried out with semi-automated hypotonic treatment, followed by TFF for purification. In the third step, microfluidizer is used to generate high shear force for membrane-core fusion. The overall process is modular, emphasizing not only the scalability and GMP-compatibility, but also the ability of integration for aseptic processing.

Preparation of Monodispersed Polymeric Nanoparticle Cores Using a Flash Nanoprecipitation Process The poly(lactic-co-glycolic acid) (PLGA) nanoparticles that make up the cores of the nanosponges are prepared via polymer self assembly through a flash nanoprecipitation method. When the polymer solution is mixed with an aqueous solution, the hydrophobic PLGA will precipitate out of the solution owing to hydrophobic interactions. The physicochemical properties of the resulting nanoparticles depend on the concentrations of the involved substances and the mixing time. Rapid mixing (short mixing time) will ensure homogeneous environment for nucleation and growth of the nanoparticles. In a previous study, PLGA nanoparticles were synthesized by direct injection of PLGA/acetone solution into water followed by solvent evaporation. To scale up the nanoparticle production, a previously developed multi-inlet vortex reaction (MIVR) was utilized to produce nanoparticle cores at large quantities. At high flow rates, turbulence promotes continuous mixing of solvent and non-solvent to create high supersaturation to initialize particle precipitation. The MIVR was previously demonstrated to produce nanoparticles at a yield of 15 g/hr, and the device can be scaled up to adapt to different production needs. By controlling the flow rates at the different inlets, fluidic dynamics within the reactor can be manipulated to yield nanoparticles of different sizes and polydispersity. The defined chamber geometry will allow calculation of the Reynolds number (Re) based on the inlet fluid velocity and viscosity. The Reynolds number will be varied to span the full range of working conditions of industrial interest, corresponding to Re of $10^3$-$10^6$. Specifically, two operation parameters will be varied to change the Reynolds number, including inlet velocity and polymer concentration, with the aim of maximizing the production rate of monodisperse nanoparticles approximately 70 nm in diameter.

Figure 7:
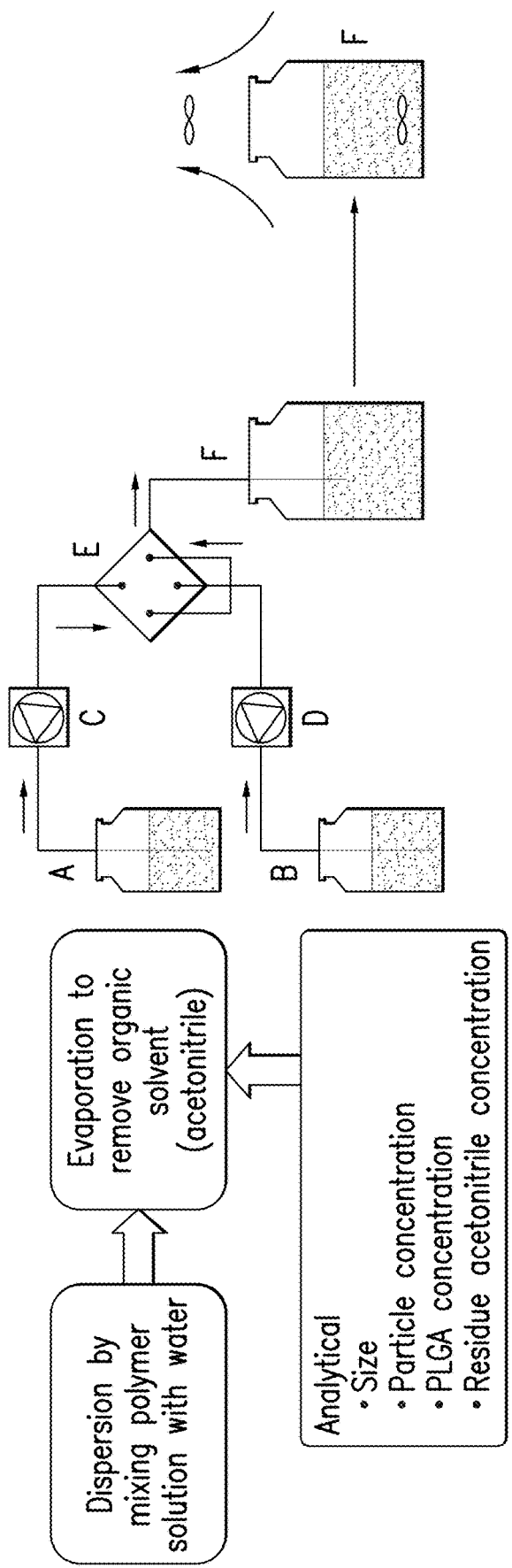
FIG. 7 illustrates two exemplary major steps and setup of making nanosponge cores and the corresponding analytical methods.

Core preparation process was developed as an independent manufacturing process, which includes two steps: dispersion and evaporation (FIG. 7). Analytical assays for this step were also identified, which include size, particle concentration, PLGA concentration, and residue acetonitrile concentration.

Figure 8:
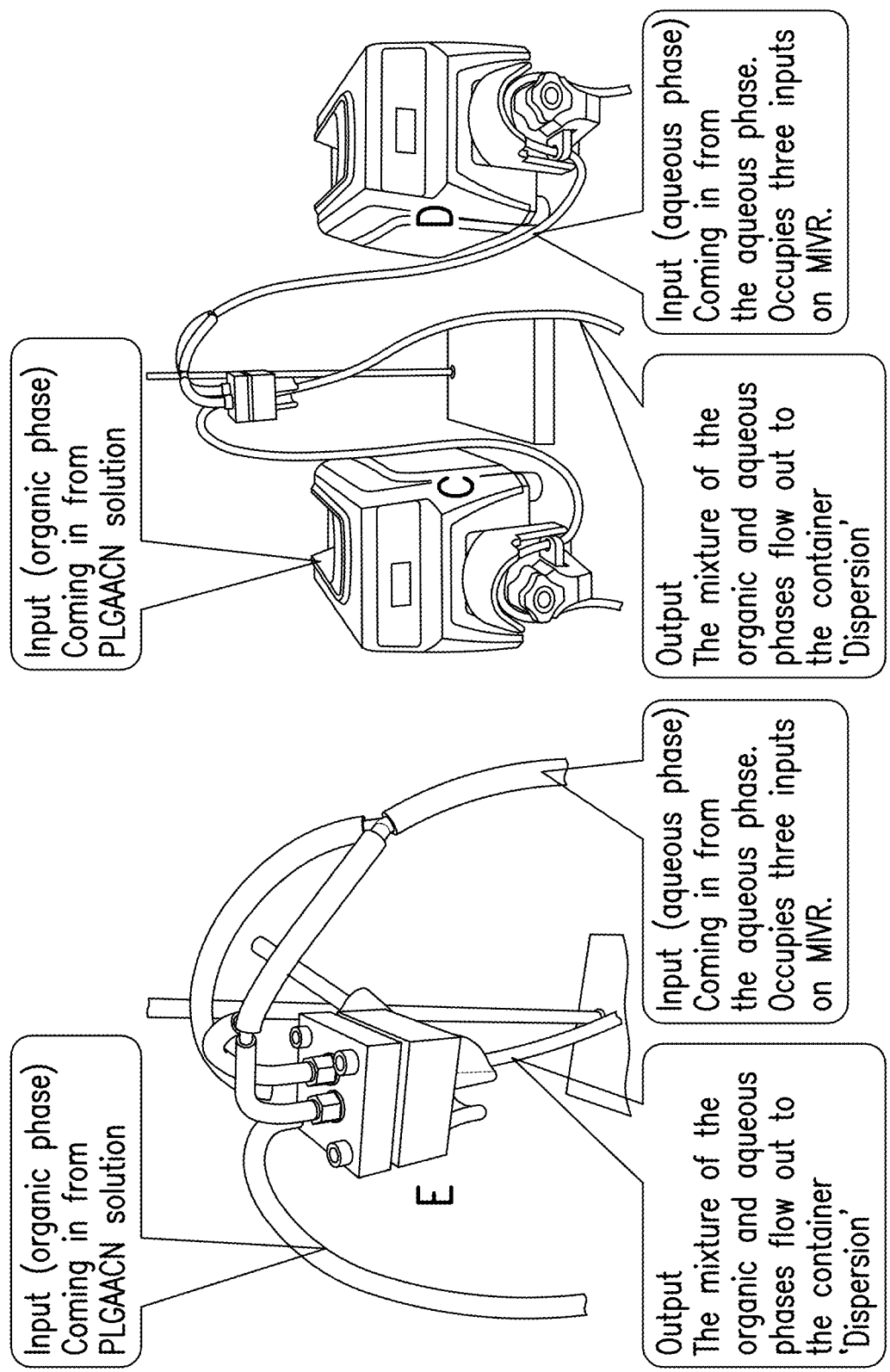
FIG. 8 illustrates an exemplary core production setup.

Current MIVR accepts 4 inlets: one assigned to organic phase (container A) and three assigned to water (container B). Two dedicated peristaltic pumps (C and D) inject liquid into the MIVR (E). A 4-L beaker is used as the dispersion container (F) to collect the mixture from MIVR (E). The process includes the following steps (FIG. 8):

Step 1. Set pump C (designated to pump organic phase, container A) to 50 rpm (equivalent to 40 mL/min, conversion based on the tubing used) (Note: RPM to flow rate conversions for various tubing can be found in the operational manual.)

Step 2. Set pump D (designated to pump water, container B) to 150 rpm (equivalent to 120 mL/min).

Step 3. Start pump D (for injecting water) and allow it to run for approximately 5 seconds. (Note: This is to prime the system and ensure the tubing was filled with aqueous solution before the injection of organic solvent.)

Step 4. Start pump C (for injecting organic phase).

Step 5. Collect the mixture from MIVR into dispersion collector (F).

Step 6. Polymer solution in container (A) will be consumed first. Keep the pumps running until water in container Bis also consumed. Then stop pump C.

Step 7. Stop pump D.

With the use of programmable peristaltic pumps, the flow rates of both organic and aqueous solutions were controlled. By analyzing the nanoparticles with dynamic light scattering, the above parameters were iteratively refined. A particle production rate of 10 g/hr (not including the time for evaporation) was achieved. The reproducibility of the process was further tested. The specification for polymeric nanoparticle cores is listed in Table 2. Exemplary records are listed, showing seven consecutive batches of polymeric nanoparticle cores with qualified specifications (Table 3). Such reproducibility suggests that the process disclosed herein is reliable for manufacturing.

TABLE 2

Analytical specifications for nanoparticle cores

| | Parameters | Specification | Method |
|---|---|---|---|
| Quantity | PLGA concentration | 1.0 ± 0.1 mg/mL | Dry and weigh |
| | Volume | 1000 ± 5 mL | Graduated Cylinder |
| Quality | Size | 70 ± 10 nm | DLS |
| | PDI | ≤0.2 | DLS |
| Impurity | Acetonitrile concentration | TBD | GC-mass |

To remove the residue organic solvent (acetonitrile), TFF was again used to replace the solvent with water and gradually filter out the organic solvent. A TFF system allows nanoparticles to flow continuously while the organic solvent molecules are filtered out via a hollow-fiber filter. In theory, a diafiltration process that replaces 5-time of total volume can remove ~99% of solutes.

TABLE 3

An exemplary batch record of polymeric nanoparticle cores

| Parameters | Specification | C161 | C162 | C163 | C164 | C165 | C166 | C167 |
|---|---|---|---|---|---|---|---|---|
| PLGA (mg/mL, Nominal) | 1.0 ± 0.1 | 1 | 1 | 1 | 1 | 1 | 1 | 1 |
| Volume (mL) | 1000 ± 5 | 1000 | 1000 | 1000 | 1000 | 1000 | 1000 | 1000 |
| Size (nm) | 65 ± 10 | 63.5 | 64.7 | 68.4 | 67.0 | 64.6 | 70.8 | 65.0 |
| PDI | ≤0.2 | 0.16 | 0.19 | 0.16 | 0.18 | 0.16 | 0.18 | 0.18 |
| Zola | .35~-50 mV | -30.7 | -29.3 | -30.9 | -29.8 | -29.5 | -29.8 | -30.0 |
| pH | 6-7 | 6.0 | 6.0 | 6.0 | 6.0 | 6.0 | 6.0 | 6.0 |

Figure 9C:
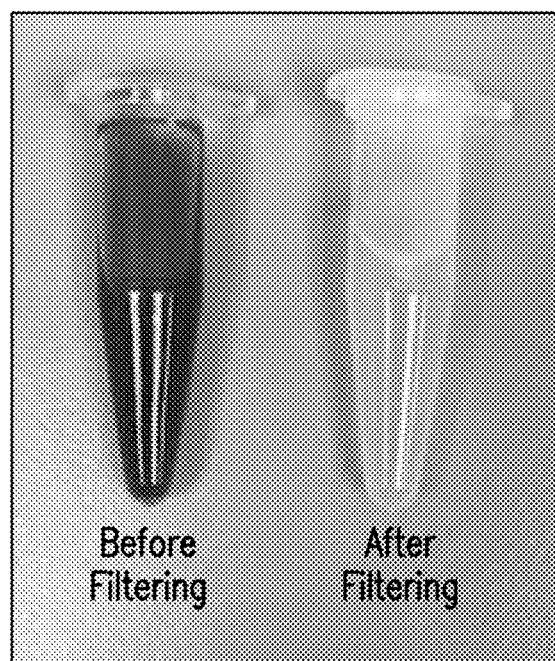
FIG. 9 illustrates an exemplary RBC membrane derivation process. (A) Schematic depicting the process of preparing RBC membrane through membrane disruption (hypotonic treatment) and TFF washing. (B) A schematic depicting RBC membrane purification via TFF. Osmotically disrupted RBCs will flow continuously through a hollow-fiber filter, which removes intracellular proteins from the RBC membrane ghosts. (C) Derivation of purified RBC membranes (right) from red blood cells (left) using the TFF system. (D) Quantification of hemoglobin content based on absorbance value reveal −99% of purification efficiency.
Figure 9D:
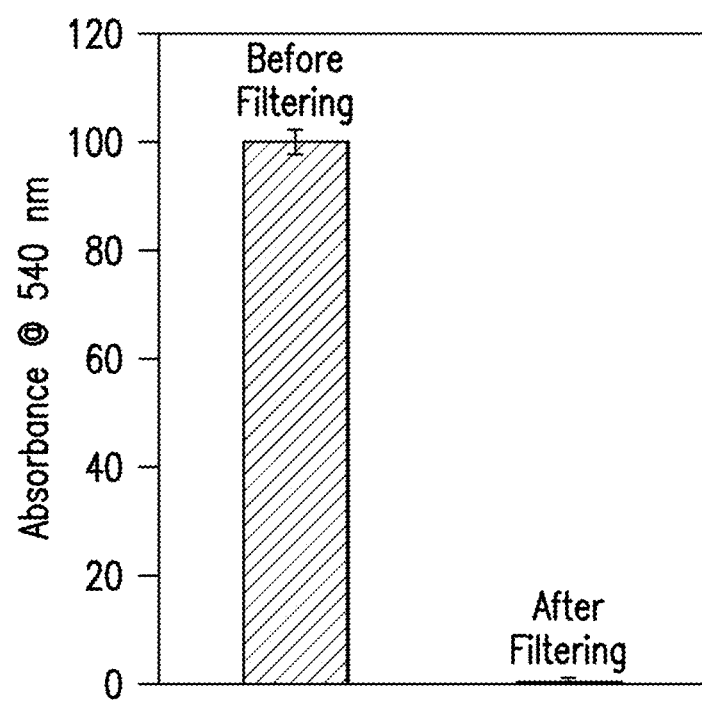

A Scalable RBC Membrane Purification Process Via a Continuous Tangential Flow Filtration Method A primary component used for nanosponge preparation is purified RBC membrane ghosts, which are RBCs deprived of their intracellular protein content. In a small-scale lab research, purification of the RBC membranes was accomplished by using a hypotonic treatment method followed by ultracentrifugation to separate RBC membranes and intracellular proteins. However, the ultracentrifugation method is not cost effective on a commercial scale and thus an alternative method for membrane separation needs to be adopted. To address this issue, a scalable manufacturing process was developed for RBC membrane preparation based on a tangential flow filtration (TFF) technique (FIG. 9). A TFF system allows RBCs and their membrane derivatives to flow continuously while their intracellular proteins are filtered out via a hollow-fiber filter. The process can be optimized to exert minimal disruption to the RBC membranes and is readily translatable for large-scale manufacturing. In one study, a KrosFlo Research Iii Tangential Flow Filtration System (Spectrum Labs, CA) was employed to develop the RBC membrane purification process. In the system, RBCs were first added to the sample reservoir. Buffer of different tonicity was then added in the sample reservoir to disrupt RBC membranes and to reseal them following the release of intracellular proteins. Subsequently, sample mixture was flowed continuously through a hollow fiber filter containing pores ranging from 500 kDa to 0.65 μm size cutoff. The porous filter allows the removal of intracellular proteins (primarily hemoglobin with a molecular weight of 64 kDa) while retaining the large RBC membranes (~5 μmin diameter).

Figure 10:
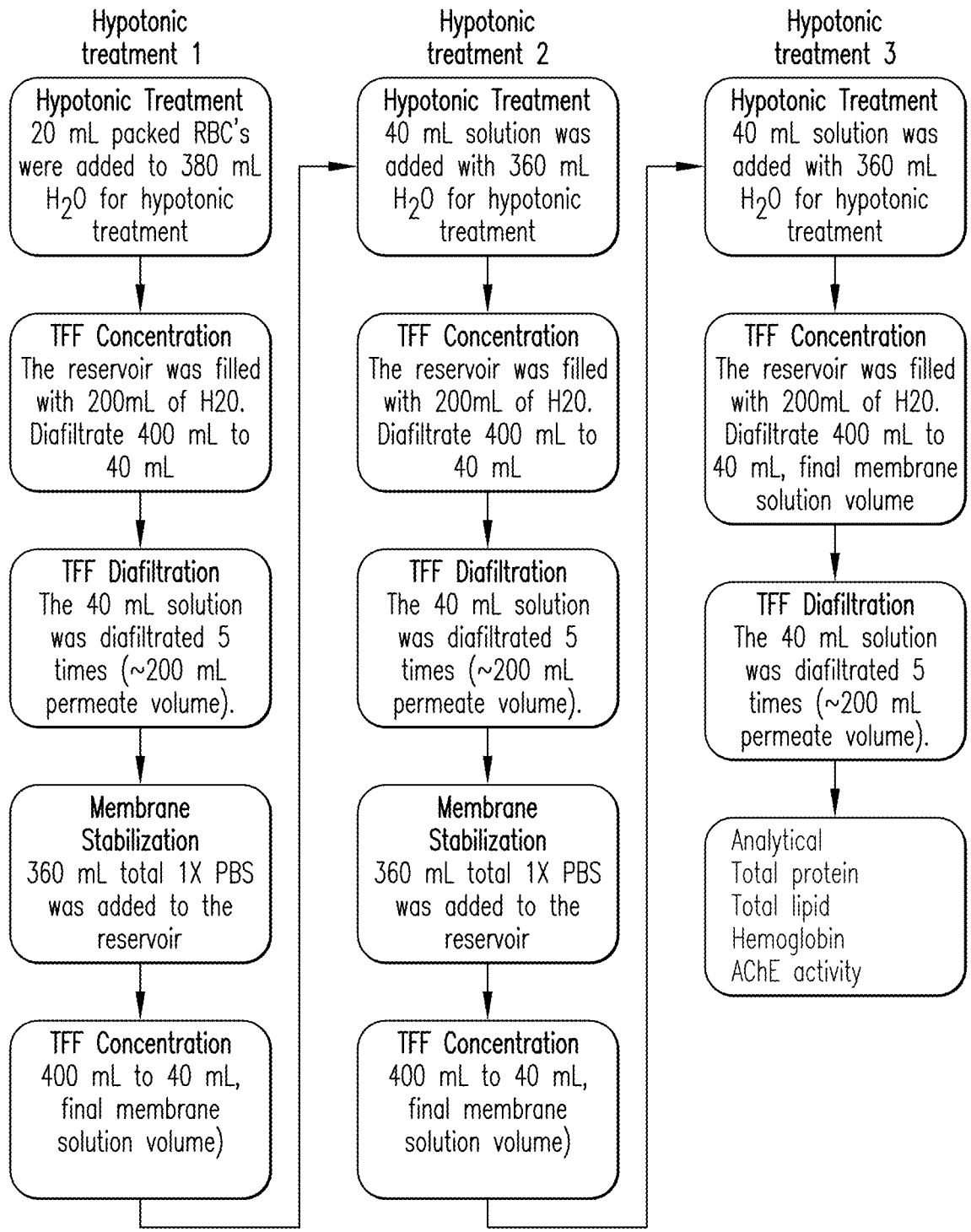
FIG. 10 illustrates exemplary major steps of manufacturing red blood cell membrane.

An exemplary membrane purification procedure has been established. The procedure is as follows (FIG. 10):

(1) Prepare 1 volume equivalent (100 mL) of 50% purified human type O RBCs in PBS with 1 mM EDTA;

(2) Add 9 volume equivalents (900 mL) of hypotonic buffer to the RBC solution to osmotically disrupt the cells;

(3) Perform the TFF process to concentrate the volume to 1 volume equivalent and diafiltrate with 5 volumes equivalents (500 mL) of hypotonic buffer to remove released hemoglobin;

(4) Reconstitute the RBC membranes in isotonic buffer by adding 9 volume equivalents (900 mL) of 1× PBS directly to the membrane mixture in the main vessel and concentrate it to 1 volume equivalent (100 mL);

(5) Repeat the hypotonic disruption by adding 9 volume equivalents (900 mL) of hypotonic buffer to the main vessel;

(6) Further filter out the released intracellular content and concentrate mixture to 1 volume equivalent;

(7) Reconstitute the sample with 9 volume equivalents of 1× PBS to the main vessel; (8) Concentrate to 1 volume equivalent and diafiltrate with 5 volumes equivalents of hypotonic buffer;

(9) Collect the resulting membrane in 1 volume equivalent of solution (100 mL).

A pressure/flow sensor is integrated to the system to monitor the different parameters of the filtration process. The sample vessel was immersed in a water bath for temperature control. Key parameters including inlet pressure, retentate pressure, transmembrane pressure, pump rate, and temperature can be optimized with the aim of maximizing the RBC membrane purification rate while maintaining yield, membrane purity, and protein activity.

The process was also optimized to accelerate the membrane preparation. In the study, operation parameters of the TFF were optimized, including flow rate, pore size, and buffer concentration. Such optimization allowed the TFF process to enhance hemoglobin release and removal from the RBC ghosts. As a result, 2 of the 3 hypotonic treatments were able to be eliminated. This achievement significantly reduced the duration of the process and produced purified membrane with the use of only 1 hypotonic treatment (FIG. 11A). To demonstrate the efficiency, various checkpoints were set during the process. At these checkpoints, a small amount of samples were withdrawn and hemoglobin concentrations were analyzed for removal efficiency (FIG. 11B). The results herein show that by the end of the process over 99.9% of hemoglobin has been removed. The purified membrane was obtained as homogeneous suspension with a faint pink hue (FIG. 11C).

In current development, two major analytic methods for membrane quality control and lot release were established. In the first method, the membrane function was tested by examining the functionality of acetylcholine esterase (AchE, a putative transmembrane enzyme on RBCs that is capable of hydrolyzing acetylcholine and used to monitor erythrocyte membrane intactness). In the second method, the membrane purity was tested by examining the hemoglobin concentration. In Tables 4A and 4B (sample analytical record of purified membrane), an exemplary sample analytic report of a batch of purified membrane is shown. The membrane sample was analyzed with an AChE assay for preservation of membrane function, and a hemoglobin assay for impurity, respectively.

TABLE 4A

Membrane function - AchE activity

| Process | AChE | U/mL | Volume (mL) | Total Unit | Recovery (%) |
|---|---|---|---|---|---|
| Hypotonic | MA31-1 | 0.230 | 1600 | 368.63 | 100.00 |
| After Concentrating | MA31-2 | 1.264 | 200 | 252.74 | 68.56 |
| After DPBS diafiltration | MA31-3 | 1.030 | 200 | 205.97 | 55.88 |
| After EDTA diafiltration | MA31-4 | 1.183 | 200 | 236.61 | 64.19 |
| Final | MA31 | 1.237 | 175 | 216.51 | 58.73 |

TABLE 4B

Impurity - Hemoglobin activity.

| Process | Hemoglobin | µ/mL | Volume (mL) | Total Unit | Recovery (%) |
|---|---|---|---|---|---|
| Hypotonic | MA31-1 | 17000.88 | 1600 | 27201.40 | 0 |
| After Concentrating | MA31-2 | 20355.96 | 200 | 4071.19 | 85.03 |
| After DPBS | MA31-3 | 1703.08 | 200 | 340.62 | 98.75 |
| After EDTA Diafiltration | MA31-4 | 256.42 | 200 | 51.28 | 99.81 |
| Final | MA31 | 255.25 | 175 | 44.67 | 99.84 |

Figure 12A:
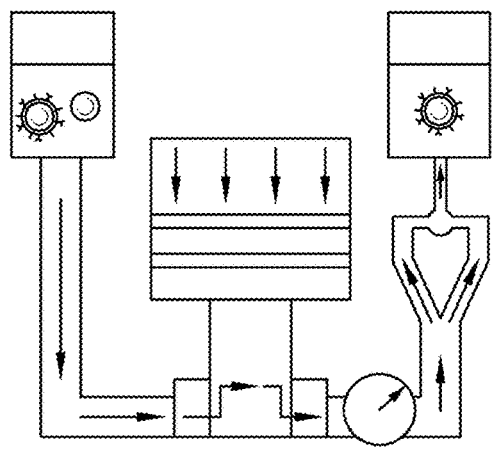
FIG. 12 illustrates (A) a schematic depicting particle/membrane fusion for nanosponge preparation using a microfluidizer. (B) Shear-induced particle/membrane homogenization will promote nanosponge formation with minimal disruption on protein activities. (C) TEM examination of nanosponges prepared from the microfluidizer. Consistent core-shell structures reflecting membrane cloaking were observed. Scale bar=100 nm.
Figure 12B:
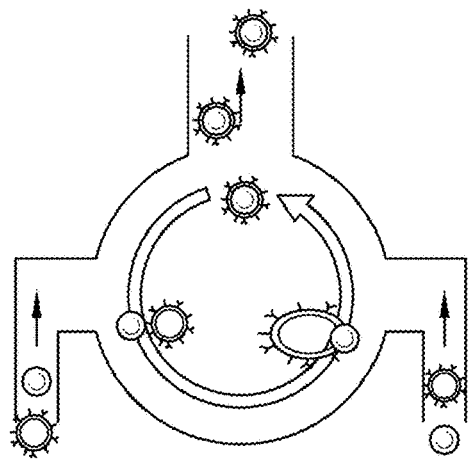
Figure 12C:
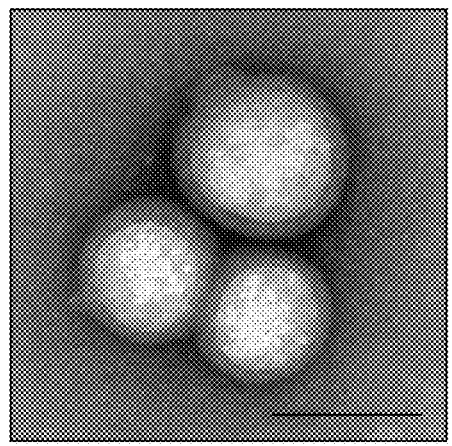

A Scalable and Non-Disruptive Particle/Membrane Fusion Process Via Shear-Induced Homogenization It was previously demonstrated that the RBC membrane cloaking process over PLGA nanoparticles is an energetically favorable process that minimizes the nanoparticle surface energy and bestows higher colloidal stability. In small-scale production, nanosponges were prepared via an extrusion process that provides a high shear force to homogenize the reaction mixture for membrane/particle fusion. In the Phase II study, a scalable and GMP-compatible homogenization process via a microfluidizer will be applied for nanosponge preparation. An LP-110 Microfluidizer (Microfluidics, Westwood, Mass.), which can provide pressure up to 30,000 psi, will be employed for the nanosponge preparation. The principle the microfluidizer is shown in FIGS. 12A and 12B. PLGA nanoparticles and RBC membrane of predetermined ratios will be passed through the microfluidizer, which will exert a high shear force in the mixing chamber to promote particle/membrane interactions. The process can be repeated to ensure complete membrane fusion. Process parameters such as pressure, flow rate, and temperature will be adjusted to optimize the formulation. It is well established that the shear-induced homogenization via microfluidizers can generate monodisperse nanoscale membrane vesicles without disrupting the activities of biological proteins.

Extrusion pressure and core membrane ratio are two key parameters that need be optimized in the fusion process. A systematic approach was adopted, including the following steps for the optimization.

First, the impact of the extrusion pressure on the pure components was examined, including the impact on polymeric cores and the membrane vesicles. The goal is to estimate the range of working pressure. To examine the impact to bare nanoparticle cores, the concentration of the core was kept at 0.5 mg/mL and the extrusion pressure was increased gradually from 0.5 to 10 kpsi. The pressure has an impact on the cores as reflected by the slight increase of the cores size (Table 5). However, there is no direct correlation between the pressure and the size increase. In addition, clogging occurred frequently when the pressure is below 5 kpsi. The results imply a suitable working range of 0-10 kpsi. Then the impact of the pressure to RBC vesicles only was examined. In contrast to the cores, vesicles extruded by the microfluidizer showed a size dependence on the pressure, as the higher pressure resulted in smaller vesicles (Table 5). Clogging was also observed with the pressure below 1 kpsi. These results together suggest a working range of 5-10 kpsi may suitable for membrane fusion.

TABLE 5

Size and size distribution of bare PLGA nanoparticle cores passing through the Microfluidizer ® at various pressures

| | Pressure (kpsi) | | | | | |
|---|---|---|---|---|---|---|
| | No processing | 0.5 | 1 | 2 | 5 | 10 |
| Size (in H$_2$O) | 70.3 | 83.3 | 83.7 | 81.5 | 77.8 | 79.3 |
| PDI (in H$_2$O) | 0.18 | 0.18 | 0.19 | 0.21 | 0.2 | 0.19 |

Next, the impact of extrusion pressure on fusion was examined. In the study, a core concentration of 5 mg/mL and a membrane-to-core ratio of 0.4:1 (membrane protein to PLGA) were kept. This ratio is based on small-scale synthesis method and will be optimized later. To evaluate the effectiveness of coating, the size increase was examined when the nanosponges are transferred from water to 1×PBS, as the high salt concentration of PBS will induce the aggregation of incompletely coated nanosponges. The results show no clogging when the extrusion pressure was above 2 kpsi (Table 6). In the range of 4-10 kpsi, nanosponges with similar sizes are obtained and they remained stable when transferred from water to 1× PBS. All measured values of polydispersivity index were no higher than 0.2. The sonication method using the same batches of the membrane and core was also compared. It was found that the microfluidizer method resulted in smaller particle sizes and narrower distribution.

TABLE 6

Size and size distribution of pure RBC vesicles passing through the Microfluidizer ® at various pressures.

| | Pressure (kpsi) | | | |
|---|---|---|---|---|
| | 0.5 | 1 | 5 | 10 |
| Size (in H$_2$O) | 167.4 | 173.6 | 155.7 | 128.4 |
| PDI (in H$_2$O) | 0.12 | 0.16 | 0.14 | 0.14 |

The core-to-membrane ratio was then optimized. The goal of this study is to determine the minimum amount of membrane needed for a given amount of nanoparticle cores to achieve full coating. Based on previous studies, the pressure herein was fixed at 10 kpsi and the core-to-membrane ratio was varied from 1:0.1 to 1:0.5. The results show that a higher membrane amount results in nanosponges with a better stability, suggesting a clear role played by the membrane in nanosponge stabilization (Table 7). Nanosponges became stable when the core-to-membrane ratio reaches 0.3 or above. Based on these results, 0.4 was recommended as a critical ratio for membrane coating.

TABLE 7

Optimization of core-membrane ratio during the fusion process

| | | 1 | 2 | 3 | 4 | 5 |
|---|---|---|---|---|---|---|
| Core-membrane ratio | | 1:0.1 | 1:0.2 | 1:0.3 | 1:0.4 | 1:0.5 |
| MF | Size (PDI) | 111.4 (0.15) | * | 98.6 (0.15) | 59.2 (0.17) | 85.4 (0.21) |
| | Size in PBS (PDI) | 213.5 (0.21) | * | 113.3 (0.13) | 99.0 (0.15) | 92.3 (0.14) |
| Soni | Size (PDI) | Crash | 112.4 (0.19) | 106.8 (0.18) | 105.3 (0.19) | 90.9 (0.17) |
| | Size in PBS (PDI) | | 317 (0.22) | 174.9 (0.16) | 122.3 (0.15) | 103.3 (0.15) |

Figure 13:
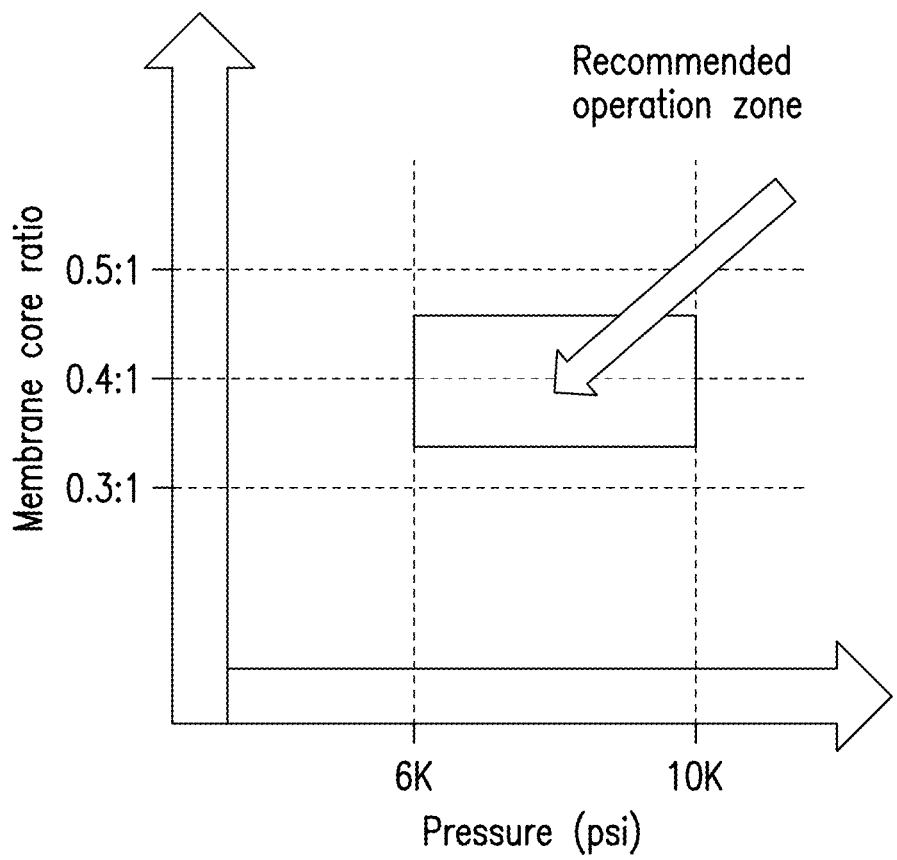
FIG. 13 illustrates optimum operation for membrane-core fusion process showing the proper working ranges of membrane-to-core ratio and pressure.

In an exemplary process, a pressure can be in the range of 6-10 kpsi and membrane-to-core ratio of 0.3~0.5:1. Exemplary results are summarized in FIG. 13.

Concentrating Nanosponges and Adjusting Buffer Conditions

Figure 14:
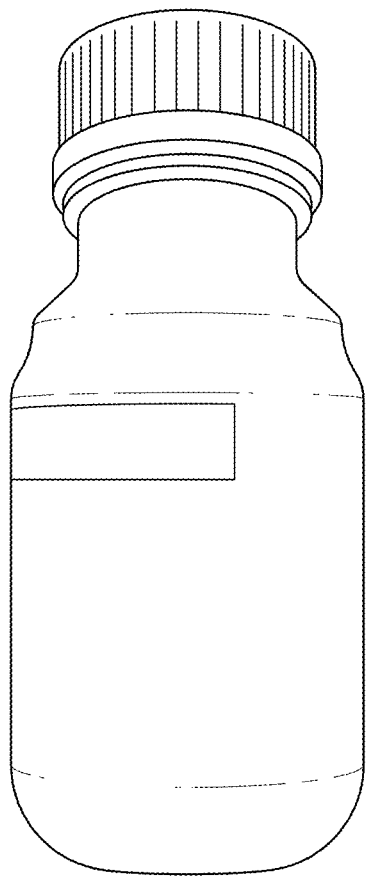
FIG. 14 illustrates exemplary nanosponges concentrated to 10 mg/mL in sucrose with TFF.

In some embodiments, the nanosponges will need to be suspended into specific buffer solutions with desired concentration. In current study, the goal is to suspend nanosponges with 10 wt % sucrose at a concentration of 10 mg/mL. To do so, 10 wt % sucrose solution was used to perform diafiltration followed by concentrating the nanosponges from approximately 0.5 mg/mL to 10 mg/mL (FIG. 14). Throughout the concentration and buffer adjustment processes, column clogging was not observed. No protein was detected in the filtrate, suggesting a complete retention of the nanosponges by the TFF. From the fluidizer, 400 mL 0.5 mg/mL nanosponge suspension was prepared, a 20× concentration (to 10 mg/mL nominal nanosponge concentration) was performed, and the solution was difiltrated with 10 wt % sucrose. The study demonstrates the robustness of the exemplary nanosponge manufacturing process.

The invention claimed is:

1. A process for preparing a cellular membrane coated nanoparticle, which process comprises mixing a nanoparticle inner core comprising a non-cellular material with a plasma membrane derived from a cell, said plasma membrane comprising a receptor activity and/or an enzymatic activity of said plasma membrane, using a high shear fluid processor to form a plasma membrane coated nanoparticle comprising said inner core and an outer surface comprising said plasma membrane, wherein said inner core supports said outer surface, and said plasma membrane coated nanoparticle substantially maintains said receptor activity and/or enzymatic activity.

2. The process of claim 1, wherein the inner core comprises a material selected from the group consisting of:
   1) a biocompatible material,
   2) a biocompatible and synthetic material,
   3) poly(lactic-co-glycolic acid) (PLGA),
   4) polylactic acid (PLA),
   5) polyglycolic acid (PGA),
   6) polycaprolactone (PCL),
   7) polylysine, polyglutamic acid, and
   8) a hydrophobic polymer that coils when switched from an organic solvent to an aqueous phase.

3. The process of claim 1, wherein the cellular membrane comprises a plasma membrane derived from a red blood cell.

4. The process of claim 1, wherein the nanoparticle substantially lacks constituents of the cell from which the plasma membrane is derived.

5. The process of claim 1, wherein the high shear fluid processor comprises a microchannel and the high shear fluid processor is configured to generate an average velocity that is up to about 500 meter/second (mis) in the microchannel.

6. The process of claim 1, wherein the high shear fluid processor is a microfluidizer or a homogenizer that generates high shear force.

7. The process of claim 6, wherein the high shear fluid processor is a microfluidizer that has the microfluidics reaction technology (MRT) configuration that comprises, from upstream to downstream, an inlet for inputting a nanoparticle inner core comprising a non-cellular material and/or a plasma membrane derived from a cell, an intensifier pump for generating a static pressure, an impinging jet chamber for generating a high shear pressure on a mixture of the nanoparticle inner core and the plasma membrane to form a plasma membrane coated nanoparticle, and an outlet for outputting the plasma membrane coated nanoparticle.

8. The process of claim 1, which is used to prepare the plasma membrane coated nanoparticle at a production rate ranging from about 0.1 g/hour to about 1,500 g/hour for one production batch.

9. The process of claim 1, which further comprises assessing the receptor activity and/or an enzymatic activity of the plasma membrane coated nanoparticle.

10. The process of claim 1, wherein the cellular membrane comprises a plasma membrane derived from a red blood cell and the nanoparticle substantially lacks hemoglobin.

\* \* \* \* \*